(12) United States Patent
Vaske et al.

(10) Patent No.: US 10,140,683 B2
(45) Date of Patent: Nov. 27, 2018

(54) DISTRIBUTED SYSTEM PROVIDING DYNAMIC INDEXING AND VISUALIZATION OF GENOMIC DATA

(71) Applicant: Five3 Genomics, LLC, Santa Cruz, CA (US)

(72) Inventors: Charles Joseph Vaske, Santa Cruz, CA (US); John Zachary Sanborn, Santa Cruz, CA (US); Stephen Charles Benz, Santa Cruz, CA (US)

(*) Notice: Subject to any disclaimer, the term of this patent is extended or adjusted under 35 U.S.C. 154(b) by 128 days.

(21) Appl. No.: 14/363,788

(22) PCT Filed: Dec. 7, 2012

(86) PCT No.: PCT/US2012/068493
§ 371 (c)(1),
(2) Date: Jun. 6, 2014

(87) PCT Pub. No.: WO2013/086355
PCT Pub. Date: Jun. 13, 2013

(65) Prior Publication Data
US 2014/0368550 A1    Dec. 18, 2014

Related U.S. Application Data

(60) Provisional application No. 61/568,478, filed on Dec. 8, 2011.

(51) Int. Cl.
*G06T 3/40* (2006.01)
*G09G 5/373* (2006.01)
(Continued)

(52) U.S. Cl.
CPC ............ *G06T 3/40* (2013.01); *G06F 19/26* (2013.01); *G09G 5/373* (2013.01); *G06F 19/22* (2013.01);
(Continued)

(58) Field of Classification Search
CPC ....................................................... G06T 3/40
(Continued)

(56) References Cited

U.S. PATENT DOCUMENTS 7,868,888 B2 * 1/2011 Dowling ............... G06T 3/403
345/471
2002/0133504 A1  9/2002 Vlahos et al.
(Continued)

FOREIGN PATENT DOCUMENTS

EP          2444914        11/2011
JP        2001125929         5/2001
(Continued)

OTHER PUBLICATIONS

Picardi etal., "ExpEdit: a webserver to explore human RNA editing in RNA-Seq experiments." Bioinformatics Applications Note, vol. 27 No. 9 2011, pp. 1311-1312,Mar. 22, 2011 (Mar. 22, 2011), p. 1311, 1312. [online] URL= <http:l/bioinformatics.oxfordjournals.org>.
(Continued)

*Primary Examiner* — Samantha (Yuehan) Wang
(74) *Attorney, Agent, or Firm* — Umberg Zipser LLP

(57) ABSTRACT

Systems and methods for dynamic visualization of genomic data are provided in which a genomic visualization system adapts presentation of information content according to scale-relevant annotations within a sequence object.

26 Claims, 27 Drawing Sheets

(51) Int. Cl.
  *G06F 19/26* (2011.01)
  *G06F 19/22* (2011.01)
  *G06F 19/28* (2011.01)

(52) U.S. Cl.
  CPC .......... *G06F 19/28* (2013.01); *G06T 2200/24* (2013.01); *G09G 2340/045* (2013.01); *G09G 2354/00* (2013.01)

(58) Field of Classification Search
  USPC .......................................................... 345/661
  See application file for complete search history.

(56) References Cited

U.S. PATENT DOCUMENTS

| | | | |
|---|---|---|---|
| 2003/0204317 A1 | 10/2003 | Loraine et al. | |
| 2004/0002818 A1* | 1/2004 | Kulp | G01N 33/68 702/20 |
| 2004/0111674 A1 | 6/2004 | Koleszar et al. | |
| 2005/0038776 A1 | 2/2005 | Cyrus et al. | |
| 2009/0125248 A1 | 5/2009 | Shams et al. | |
| 2010/0281401 A1* | 11/2010 | Tebbs | G06F 19/00 715/760 |
| 2010/0286994 A1 | 11/2010 | Tebbs et al. | |
| 2012/0066601 A1* | 3/2012 | Zazula | H04N 21/854 715/733 |
| 2012/0102041 A1* | 4/2012 | Park | G06F 19/28 707/741 |

FOREIGN PATENT DOCUMENTS

| | | |
|---|---|---|
| JP | 200665501 | 3/2006 |
| JP | 2013531980 | 8/2013 |
| WO | 2011149534 A2 | 12/2011 |

OTHER PUBLICATIONS

Koboldt, "MassGenomics." MassGenomics.org, posted Jul. 24, 2009 (Jul. 24, 2009), p. 1 4,5 [online] URL=<http:J/massgenomics.org/2009/07/sam-bam-thank-you-maam.html>.

ISA/US, International Search Report and Written Opinion for International Application No. PCT/US2012/068493, dated Feb. 21, 2013, 8 pages.

Skinner et al., "JBrowse: A next-generation genome browser" Genome Res.; 2009 (published online Jul. 1, 2009); vol. 19; p. 1630-1638. Entire document, especially p. 1630, col. 1 para 3; p. 1634, col. 1, para 1.

* cited by examiner

DISTRIBUTED SYSTEM PROVIDING DYNAMIC INDEXING AND VISUALIZATION OF GENOMIC DATA

This application claims the benefit of U.S. provisional application with the Ser. No. 61/568,478, which was filed Dec. 8, 2011. This and all other extrinsic materials discussed herein are incorporated by reference in their entirety.

FIELD OF THE INVENTION

The field of the invention is computational genomics, especially as it relates to dynamic graphic representation of complex genetic information.

BACKGROUND

The following description includes information that may be useful in understanding the present invention. It is not an admission that any of the information provided herein is prior art or relevant to the presently claimed invention, or that any publication specifically or implicitly referenced is prior art.

With the advent of high-throughput sequencing and the availability of entire genome data sets, sequencing speed is no longer the bottleneck in genome analysis but data storage, retrieval, and coordinated analysis. The difficulties associated with data storage, retrieval, and analysis are further compounded by the varying requirements for displayed information from different users. Viewed from a different perspective, information-dense and selective presentation of genomic data is paramount to making use of the massive quantity of data now available.

While there are several genomic browsers known in the art, all of the known browsers have substantial difficulties. For example, the UCSC Genome Browser (http://genome.ucsc.edu) provides massive data in a graphical forma, however, fails to accommodate to a user specified information density as predefined displays that are independent of the zoom level. Therefore, such browsers are unable to respond optimally to requests at all zoom levels. Similarly, graphic viewers like that of NCBI (http://www.ncbi.nlm.nih.gov/nuccore/) are also limited to certain predefined parameters and thus fail to allow for dynamic presentation and adaptation of content.

Consequently, even though various systems and methods of display of complex genomic information are known in the art, numerous disadvantages nevertheless remain. Therefore there is still a need to provide improved devices and methods for graphic representation of complex genetic information, and especially dynamic graphic representation.

SUMMARY OF THE INVENTION

The inventive subject matter is directed to methods and devices for dynamic visualization of genomic data in which a genomic visualization system adapts presentation of information content according to scale-relevant annotations within a sequence object. Thus, adaptive content display can be achieved at significantly reduced data analysis and transfer.

In one especially preferred aspect of the inventive subject matter, a genomic visualization system is contemplated comprising an indexed genomic database that stores a sequence object representative of a genomic region. Most typically, the sequence object includes a plurality of scale-relevant annotations. A scaling engine is coupled with the indexed genomic data storage and is configured to (a) adjust scale-relevant information derived from the scale-relevant annotations of the sequence object as a function of a user selected zoom level, (b) dynamically generate a genomic display object representative of the scale-relevant information based on the zoom level, and (c) configure an output device to present the genomic display objects to a user.

While not limiting to the inventive subject matter, it is generally preferred that the sequence object has a SAM/BAM or BAMBAM format, and/or that the genomic region is a whole genome, a chromosome, a chromosomal fragment, or an allele.

With respect to the scaling engine it is contemplated that one or more bamservers and/or visualization servers may operate as the scaling engine. Furthermore, it is contemplated that the scaling engine may be further configured to adjust the scale-relevant information by downsampling based on the zoom-level (wherein downsampling may be a function of data density derived from the zoom-level). Alternatively, or additionally, it is contemplated that the scaling engine is configured to determine the zoom level, and optionally to summarize a full data set of the sequence object according to the zoom level. Where desired, the scaling engine may also be configured to derive the scale relevant information from differences in scale-relevant annotations in different sequence objects.

In still further contemplated aspects, the sequence object comprises a reference sequence object, which is most preferably raw sequence data, sequence data from homo statisticus, and/or sequence data from a specified point in time. Alternatively, or additionally, the sequence object comprises a differential sequence object with respect to a reference genomic region (e.g., reference genomic region from homo statisticus or to a specific point in time). Similarly, the scale relevant annotations may vary considerably and will preferably include genomic structure information (e.g., chromosome identification, location within a chromosome, allele, etc.), genomic change information (e.g., a mutation, a translocation, an inversion, a deletion, a repeat, and a copy number), disease information (e.g., type of disease, a status of disease, and a treatment option for the disease), gene relevant information (e.g., raw sequence data or processed sequence data, gene identification, information on gene regulation, and information of association of the gene with a disease), differential information relative to a reference sequence, and/or metadata (e.g., patient identification, facility identification, physician identification, and insurance information).

While not limiting to the inventive subject matter, it is generally preferred that the genomic visualization system will further include a genomic graphic library that stores a graphic object representative of scale relevant annotations. In such systems, it is particularly preferred that the scaling engine maps the scale relevant information to graphic objects from the graphic library according to the zoom level, and that the genomic display object comprises the mapped graphic objects. With respect to suitable output devices, a display, a browser, a printer, a 3D printer, and/or a speaker are typically preferred.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
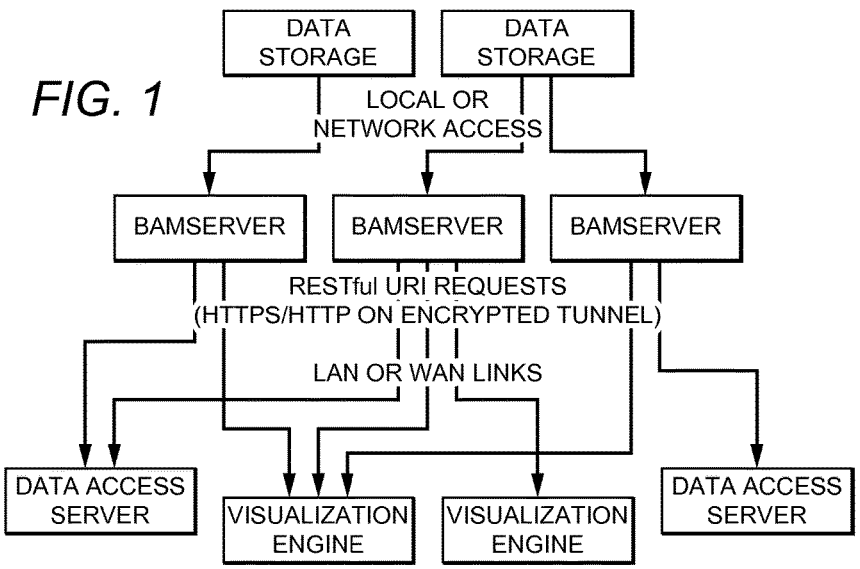
FIG. 1 provides an overview of a distributed genomic visualization environment.

The inventive subject matter is directed to devices and methods for dynamic visualization of genomic data. Contemplated systems and methods allow for selective and scalable display of information-rich content while reducing data aggregation and traffic.

It should be noted that while the following description is drawn to a computer/server based genomic visualization systems, various alternative configurations are also deemed suitable and may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Contemplated devices and methods combine advantageous features of a bamserver and a genome visualization engine that are loosely coupled such as to allow for trivial integration with other alternative genomic powered engines or other genomic data storage solutions. In addition, each component can scale as necessary to accommodate multiple bamservers or multiple visualization engines, as schematically and exemplarily illustrated in FIG. 1. Most preferably, each server is flexible enough to maintain independent storage, authentication, and data retrieval on its own as well as in a distributed nature where each server may coordinate some parts with other servers. Moreover, the ability of both the bamserver and visualization engine to dynamically scale the data provided from large data sources will help mitigate against significant increases in data sizes of future data formats and file types.

Figure 2:
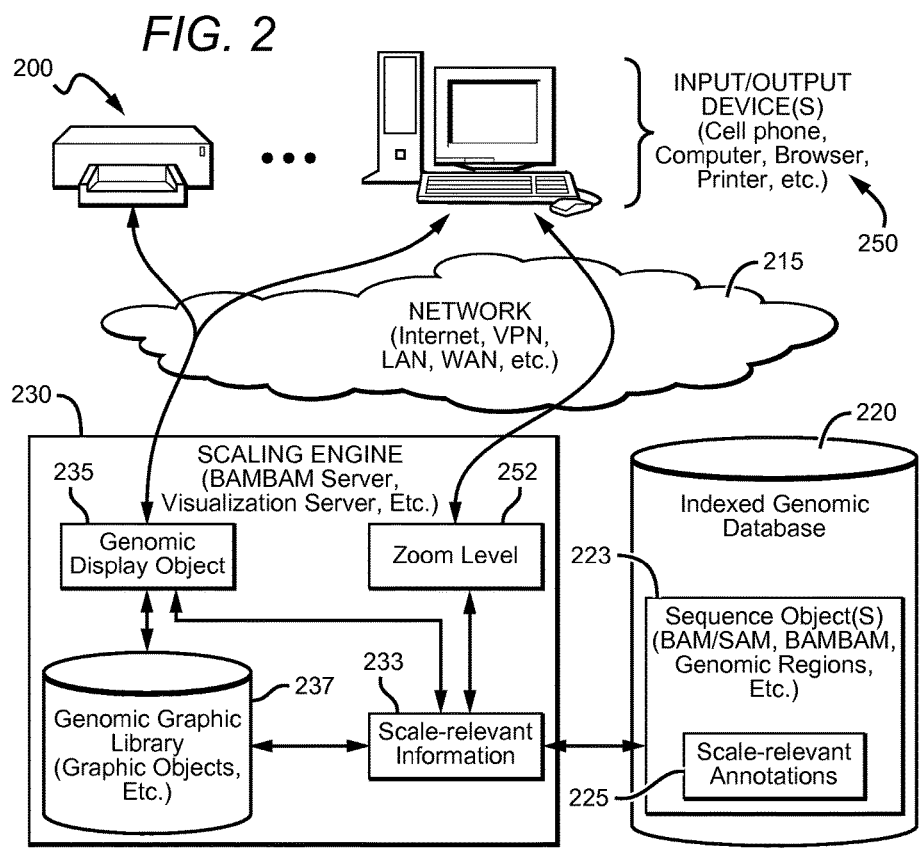
FIG. 2 illustrates a possible genomic visualization system including a visualization scaling engine.

FIG. 2 illustrates genomic visualization system 200 capable of generating a visual display of genomic information a different scales of observation. System 200 includes indexed genomic database 220 and scaling engine 230. In some embodiments, system 200 can also include genomic graphics library 237 or even devices 250, possibly operating as clients of the services offered by system 200. For example, devices 250 can include a browser-enabled computing device (e.g., a cell phone, tablet, computer, etc.), through which a healthcare provider or a patient can access genomic information of interest over network 215. Scaling engine 230 can provide a visual display of the genomic information to the user's browser via HTTP, or other suitable protocol.

It is generally contemplated that a genomic visualization system 200 will comprise an indexed genomic database 220 that stores one or more of sequence objects 223 representative of a genomic region, wherein the sequence object 223 includes a plurality of scale-relevant annotations 225. Scaling engine 230 is coupled with the indexed genomic database 220 and configured to adjust scale-relevant information 233 that is derived from the scale-relevant annotations 225 of the sequence object 223 as a function of a user selected zoom level 252. The scaling engine 230 will then dynamically generate a genomic display object 235 that is representative of the scale-relevant information 233 based on the zoom level 252, and configure an output device 250 to present the genomic display objects 235 to a user.

As used herein, the term "genomic region" typically refers to a sequence name and a start and end coordinate that specify a closed interval within that sequence. An example genomic region is: chr1:1234-5678, where chr1 specifies the sequence of chromosome 1 from a human reference genome, 1234 is the start coordinate, and 5678 is the end coordinate. However, it should be readily apparent to the person of ordinary skill in the art that the particular format of the genomic region may vary considerably and that suitable formats will include particular references to the chromosomal location and/or sub-location, to gene names or functions, regulatory aspects of the gene(s) in the region, chromatin structural aspects of the gene(s) in the region, length of sequence, etc. Therefore, and viewed from a different perspective, the genomic region may be a whole genome, a chromosome, a chromosomal fragment, or an allele. Moreover, it should be noted that specification of multiple genomic regions in a single request is possible by using any known delimiter between the genomic regions.

Consequently, it should be recognized that the sequence object 223 may have numerous data formats, and that all known formats are deemed suitable so long as such formats also include one or more scale-relevant annotations. For example, particularly preferred formats for contemplated sequence objects include SAM/BAM and BAMBAM format. Likewise, it should be appreciated that the sequence object 223 may represent a genomic region of a reference genome (e.g., from homo statisticus) or a genomic region of a test sample. Where the sequence object 223 is from a test sample to be analyzed, it is typically preferred that the analysis is performed with respect to a reference genome and/or a genome of the same test subject from a different point in time. Thus, suitable reference sequence objects 223 may include raw sequence data, sequence data from homo statisticus, and/or sequence data of a test subject from a specified point in time. Moreover, it should be recognized that the sequence object 223 need not necessarily be confined to a raw data read or assembled sequence (e.g., full-length gene), but that the sequence object 223 may be or comprise a differential sequence object 223 with respect to a reference genomic region (e.g., in which only discordant corresponding bases are listed). As before, such reference genomic region may be from the same test proband taken at an earlier point in time, or from an actual healthy proband or a hypothetical, consensus sequence from multiple healthy probands (homo statisticus).

With respect to scale relevant annotations 225 it is contemplated that the annotations 225 may vary considerably and that all annotations known in genomics analysis are deemed suitable for use herein. For example, particularly preferred annotations 225 include those related to the genomic structure on various scale levels (e.g., location of sequence on a chromosome, location within a chromosome, allele information, etc.) and those related to genomic changes on various scale levels (e.g., chromosomal translocation, repeat or copy number, insertions, deletions, inversions, various mutations such as SNPs, transitions, transversions, etc,). Likewise, scale relevant annotations 225 may also include disease information on various scale levels (e.g., polyploidy, copy and/or repeat numbers, type/status/ treatment options of a disease associated with mutations or copy numbers, etc.). In further contemplated aspects, the scale relevant annotations 225 may also include gene relevant information on various scale levels (e.g., gene as part of a functional or regulatory network of genes, gene name or functional identification, raw sequence data or processed sequence data, gene identification, information on gene regulation, and information of association of the gene with a disease).

Of course, it should be appreciated that all or part of the relevant information may also be expressed as differential information relative to a reference sequence (e.g., homo statisticus or earlier point in time), which will advantageously reduce data size and complexity. Additionally, scale relevant annotations 225 will typically also include metadata associated with the sequence object, and most typically include patient identification, facility identification, physician identification, and/or insurance information.

Viewed from a different perspective, scale relevant annotations 225 will include annotations that are suitable for display for selected audiences (e.g., physician, researcher, patient, insurance, etc.). For example, where the audience is a physician, scale relevant annotations 225 may be relevant to a display format of an entire genome in simplified format (e.g., circle plot, metaphase spread, etc.) where mutations are indicated by simple pointers or other graphical tools. On the other hand, where the audience is a researcher, scale relevant annotations 225 may be relevant to a display format in which actual raw sequence data and copy number/allele frequency is provided.

Moreover, and regardless of the audience, it should be recognized that the type of visual presentation will dynamically change as a function of zoom level 252 such that appropriate content relative to the zoom is displayed. Consequently, scale relevant annotations 225 may further include data that indicate suitability for the particular annotation for a specific zoom level or levels 252. Of course, suitability for display at a given zoom level may also be determined independently of such data as further discussed below. Zoom level 252 selected by a user can be determined through various techniques. In some embodiments, zoom level 252 can be determined based on the user profile: healthcare provider, patient, insurance company, researcher, or other type of profile. For example, zoom level 252 representing a highest level zoom (i.e., maximum view of the genomic region) can be selected as a default when a patient is viewing the data. Alternatively, a researcher might have a default zoom level 252 that targets specific regions of interest. Other techniques for establishing zoom level 252 include receiving a user selected bounding box from the visualization device (e.g., browser, application, etc.), automatically triggering on anomalous genomic regions relative to a reference region (homo statisticus), receiving genomic information from a sequence device indicative of a region of interest, or other techniques.

There are numerous options to graphically represent the scale relevant annotations 225 and it is especially preferred that graphic representation is performed using known symbols and notations. Most preferably, known symbols and annotations can be stored in a genomic graphic library 237 that is configured to store graphic objects representative of the scale relevant annotations 225. In such case, it is particularly preferred that the scaling engine is configured to map the scale relevant information 233 to graphic objects from graphic library 237 according to the zoom level 252, and that the genomic display object 235 comprises the mapped graphic objects. For example, scaling engine 230 receives zoom level 252 from a healthcare provider who is reviewing a patient's genomic information with respect to known mutations. Scaling engine 230 obtains sequence object 223 from indexed genomic database 220 along with the associated scale-relevant annotations 225. Scaling engine 230 derives scale-relevant information 233 as a function of the scale-relevant annotations 225, the healthcare provider information (e.g., authorization, profile, etc.), and zoom level 252. Scale relevant information 233 thus represents the genomic region of sequence object 223 at a proper zoom level as well as at an appropriate level of detail with respect to the observer. In other words, at the given level of zoom, the scale-relevant information 233 represents the information that would be appropriate for the healthcare provider. If the observer were a patient, scale relevant information 233 would likely carry a different presentation of the genomic information the would be appropriate for the patient even though zoom level 252 and sequence object 223 are identical. Scaling engine 230 then maps the scale relevant information 233 to one or more graphic objects in genomic graphic library 237 to create genomic display object 235.

One should appreciate that genomic graphic library 237 is configured to store genomic graphic objects rather than mere graphic primitives. Genomic graphic library 237 can be updated with additional genomic graphic objects as desired or existing genomic graphic objects can be modified, possibly with different graphics (e.g., textures, skins, themes, etc.). Such an approach is considered advantageous within the market as it allows for branding or customization of visual presentations.

With respect to hardware it should be noted that contemplated devices and methods may be configured and operated in numerous manners, and it should be appreciated that the particular configuration and/or manner of operation will at least in part dictate the functional components and interconnections. Thus, the following description of preferred aspects should only be viewed as exemplary guidance to the person of ordinary skill in the art.

With respect to suitable bamservers it is generally preferred that the bamserver is or comprises a distributed network server system capable of efficient random access to data indexed by genomic region, supporting protected access to encrypted data both over secured connections and via encrypted file access. In a typical use case, a user will: 1. connect to the bamserver over the network, 2. issue a request with two parameters—A) a data archive and B) a list of genomic regions, and 3. receive all data entries from the archive that overlap any of the provided genomic regions. As used herein, the term "data archive" refers to a set of data entries where each entry is associated with a genomic region. A data entry can be any data, including a single number, a string of characters, and a list of numbers and/or strings. Some common examples of data entries are a sequence read and associated read quality from a sequencing machine, a known gene location, or a detected mutation.

Indexing genomic regions: When a data archive is added to the bamserver, the bamserver sorts the data entries by genomic region, then preferably creates an R-tree like binning index, as is commonly used in genomic applications and has been described fully in its use in the UCSC Genome Browser and the SAM Tools software library. Briefly, an indexed sequence is broken up into overlapping bins. Starting with one bin covering the entire sequence, two new bins are added which split the previous bin in half. The index then has pointers from each bin to the data entries that fit within that bin, but no smaller bin. Retrieving data entries that overlap a query is then a matter of examining only the bins that overlap the query.

Data access protections: Most typically, the bamserver restricts access to non-public data archives by checking each request against a data file access server. If the client does not provide sufficient security credentials according to the data file access server, access to any results are denied. Each bamserver can be configured for a unique data file access server, allowing flexible permission schemes and federated authentication methods.

With respect to data storage it is generally contemplated that the data archives of the bamserver are stored on a file system that appears local to the bamserver. This file system may use disks attached directly to the bamserver and/or network-accessible disks. It is further preferred that protected data archives are stored in an encrypted form (e.g., AES symmetric block encryption, using CTR mode). The bamserver will typically not have access to the encryption key. When processing a request for a protected data archive, if the data file access server grants access, the data file access server will provide the encryption key for the requested file. The bamserver will use the key while processing the request, and discard the key as soon as the request is completely processed.

Suitable request methods are typically made using RESTful (conforming to representational state transfer constraints) queries over HTTPS, an SSL-secured HTTP protocol, or using an alternative encrypted tunneling mechanism within which HTTPS queries are made. The RESTful nature of the queries allows bamservers to be distributed both geographically and locally to provide maximum throughput to consuming applications. The only constraint on locality of the bamserver is direct file access to the underlying data, which could even be presented over a wide-area network using the appropriate protocols (NFS over VPN, or other such solutions).

In further preferred aspects, dynamic scaling of the data is implemented. Based on the size of the genomic region requested and knowledge about the resolution with which the data will be displayed, the bamserver, possibly operating as scaling engine 230, has capabilities of dynamically scaling ("downsampling") the data to provide a more condensed version that will reduce processing and transfer times. This downsampling is most preferably accomplished in two parallel mechanisms. The first mechanism requires no knowledge of the underlying data, and is accomplished by providing the bamserver files that are pre-condensed to certain levels. The bamserver can then dynamically decide at the time of query if it should provide a "raw" level of data, or alternatively one of the condensed files. This decision is made by including an additional parameter in the request that indicates the number of data points that will be utilized by the consuming application. If the consuming application is a visualization engine, which could also operate as scaling engine 230, one example of a useful data point count might be based upon the number of pixels that will be drawn to the screen. The second mechanism for downsampling is dynamic summarization of the full data accessible to the bamserver. This mechanism requires providing additional information about the file type to the bamserver so that it can understand which fields are possible to summarize, and the mechanism of summarization. Given a file with only a single data column beyond the genomic coordinate index, this could be automatically determined and a median or mean summarization could automatically be performed. For more complex data types or more complex summarization techniques, the bamserver will require parameters outlining how to perform that summarization. One example is downsampling of a file in SAM/BAM format, which would perform a downsampling by sub-sampling the individual reads at each position, only providing a limited number back to the consuming application.

It should further be appreciated that contemplated systems and methods are readily extensible as the bamserver is capable of reading files from multiple formats and understanding both genomically indexed data and additional storage formats such as SQLite and JSON. The format of the requested file is currently provided by the consuming application, but auto-detection of file format is also contemplated. The architecture of the bamserver preferably supports additional data formats in the form of plugins that can understand foreign indexing schemes and still provide a unified interface. These plugins are either specified via the universal resource identifier (URI) REST request, or by auto detection of the appropriate format within the bamserver.

With respect to dynamic genome visualization engines, it generally contemplated that a dynamic genome visualization engine is capable of interpreting multiple types of data with the common attribute of being mapped to a location in the genome, and producing image-based interpretations of the data. It should be noted that the concept of a genome "browser" in some sense is already known (e.g., University of California, Santa Cruz Genome Browser, established in 2001 (see URL genome.ucsc.edu)). However, currently known browsers limit views of data to user specified densities and are unable to respond to requests past certain limits in a timely and meaningful manner. In contrast, the dynamic genome visualization engine contemplated herein is capable of understanding the amount of data being requested by a user and altering the visualizations presented to provide more compact and summarized versions when appropriate. At one level, the level of downsampling is handled by the bamserver, which understands the region that is attempting to be visualized, and will automatically reduce the data sent to the visualization engine. At a higher level, if the engine itself recognizes a sufficiently large amount of data is being request, the underlying visualizations produced will alter in a way to provide summaries that are more useful to the end-user.

Figures 1, 3:
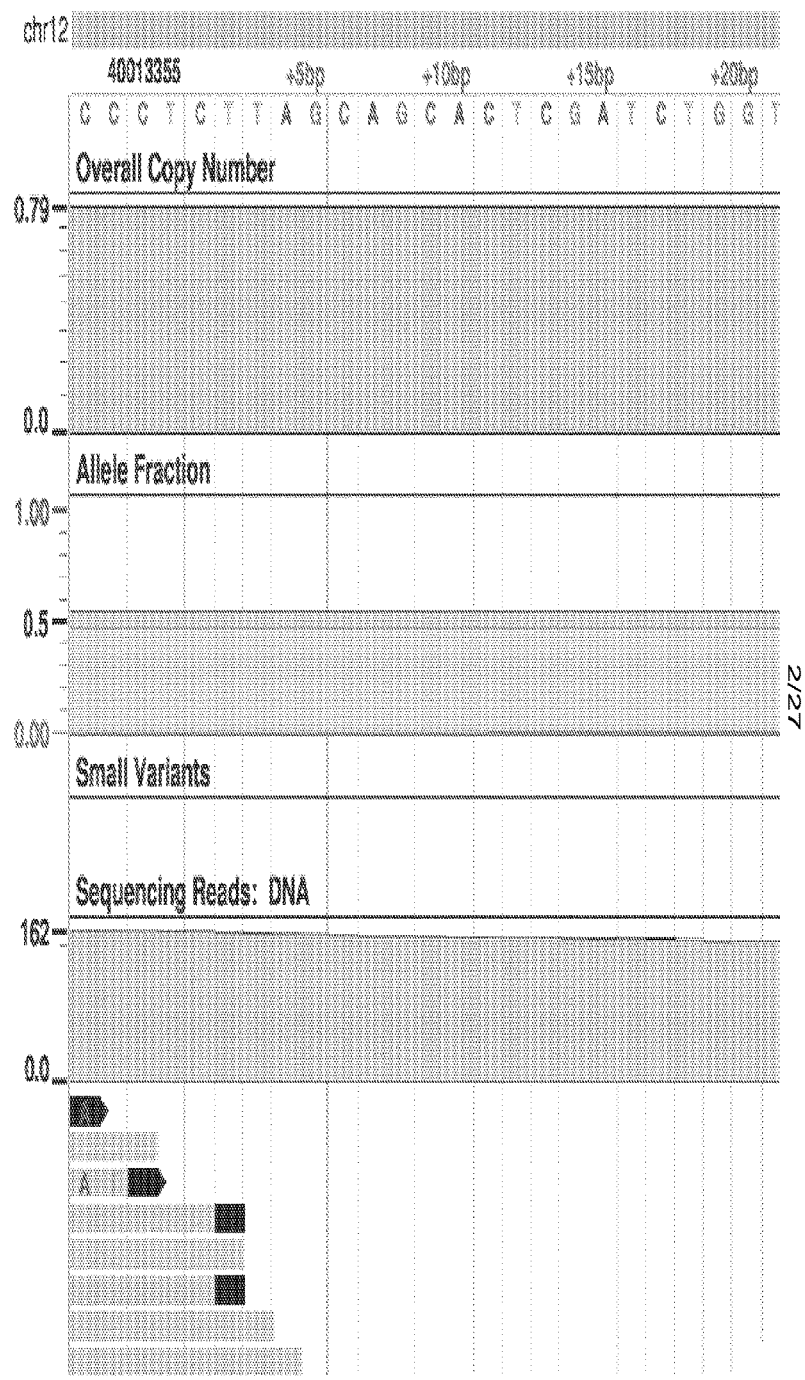
FIG. 3 is an exemplary display view at base zoom level.
Figures 2, 3:
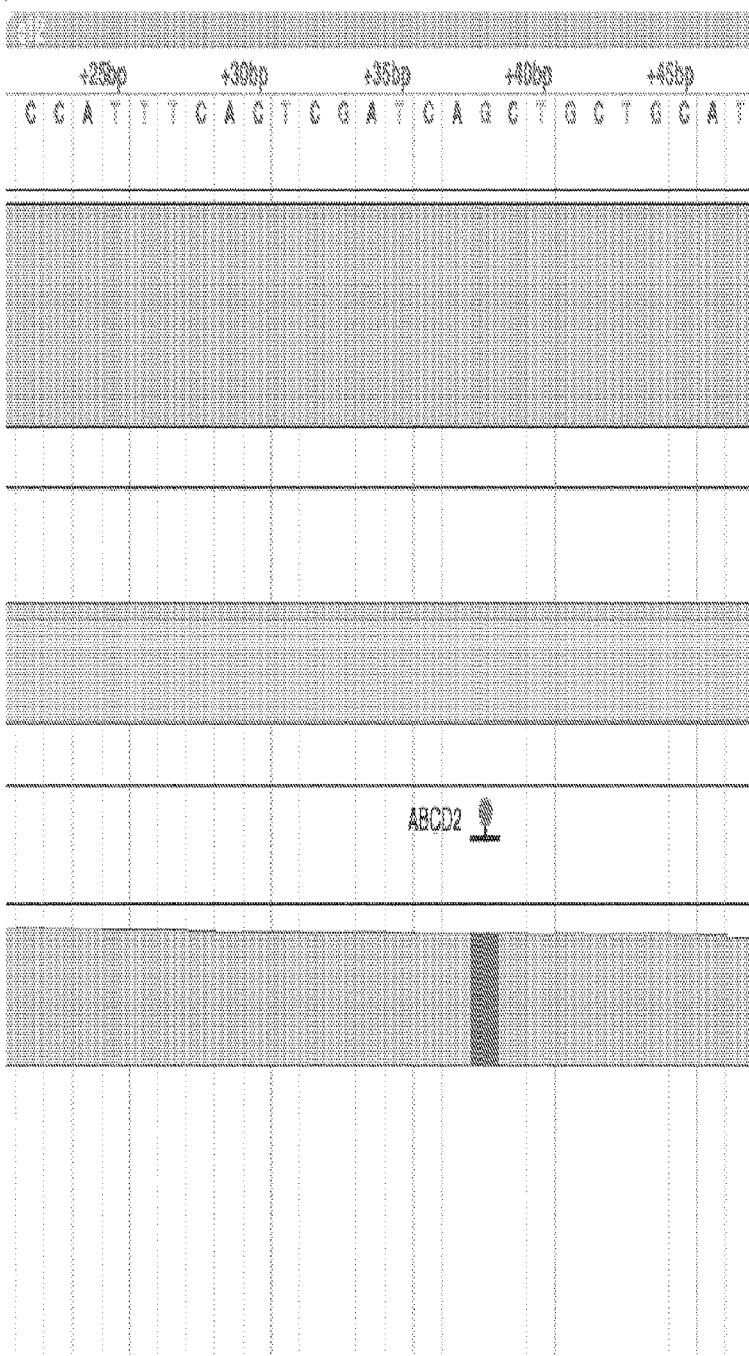
Figure 3:
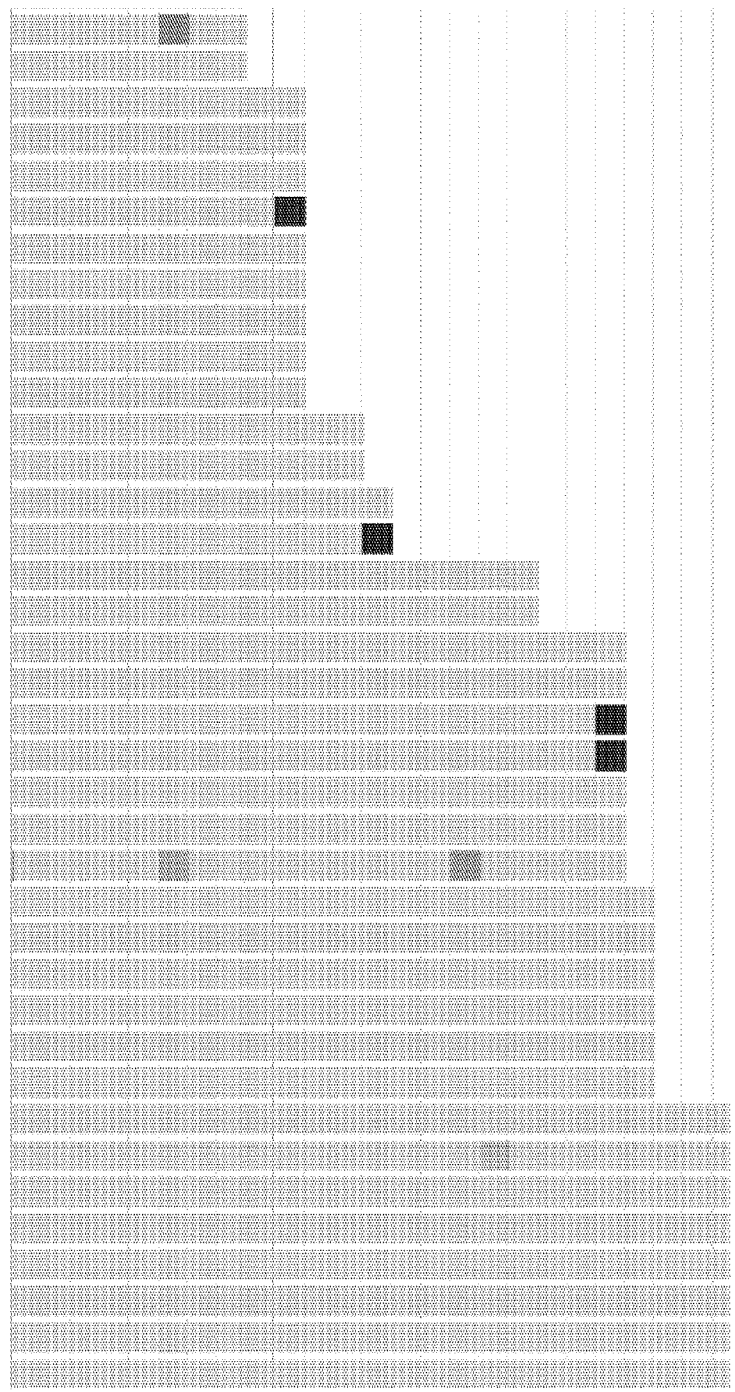

Displays can vary widely based on the density of data attempting to be viewed. FIGS. 3-6 represent some examples of how these display change based on the various number of bases the user is viewing in the window where the displays are generated from genomic graphic objects used to generate genomic display objects 235 within a browser. It is important to emphasize that these displays are dynamically generated and not pre-computed, although for certain use cases pre-generated static images are not excluded and are supported by contemplated devices and methods. In FIG. 3, 52 bases of the human genome are shown across approximately 1000 horizontal pixels, with graphical representations of overall copy-number, allele specific copy-number, raw sequencing data from BAM, and an annotation track of UCSC Known Genes. Each of these tracks is pulled dynamically from the bamserver architecture outlined earlier, and each track can query an independent bamserver to obtain the data necessary. Because such a small number of bases are being shown, no downsampling on either the bamserver or the visualization engine is being performed. Thus, it is particularly preferred that the lowest zoom level is at the base readout of the raw or computed sequence.

Figures 3, 4:
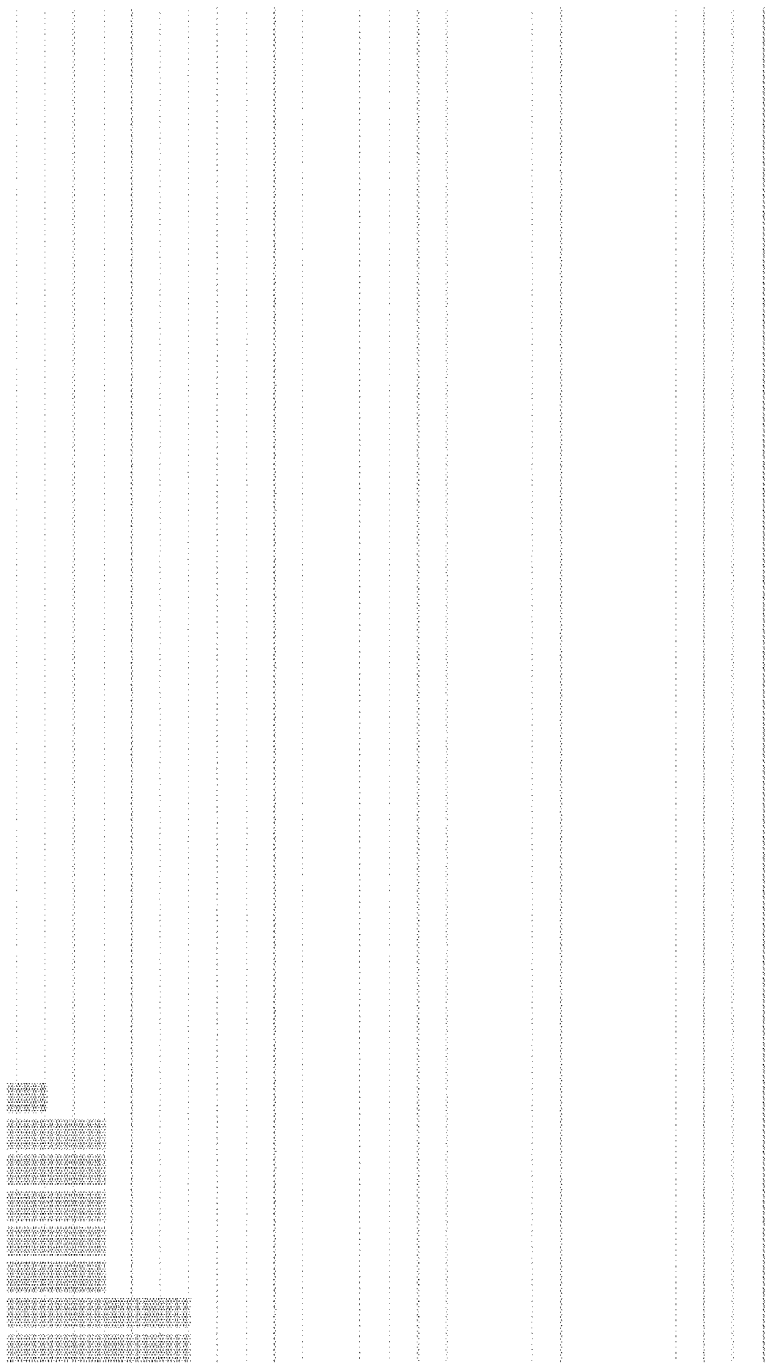
FIG. 4 is the exemplary display view of FIG. 3 at a sub-kilobase zoom level.

FIG. 4 represents a sub-kilobase zoom level showing about 1000 bases from that same region of the genome. At this resolution and number of bases, no downsampling is taking place on the bamserver, however the visualization engine has begun to alter the display of each data source to accommodate the increased viewport. In particular, the letters on each base no longer appear both on the top reference base bar and within the individual bam reads, instead resorting to simple colors to represent the changes identified.

Figures 3, 4, 5:
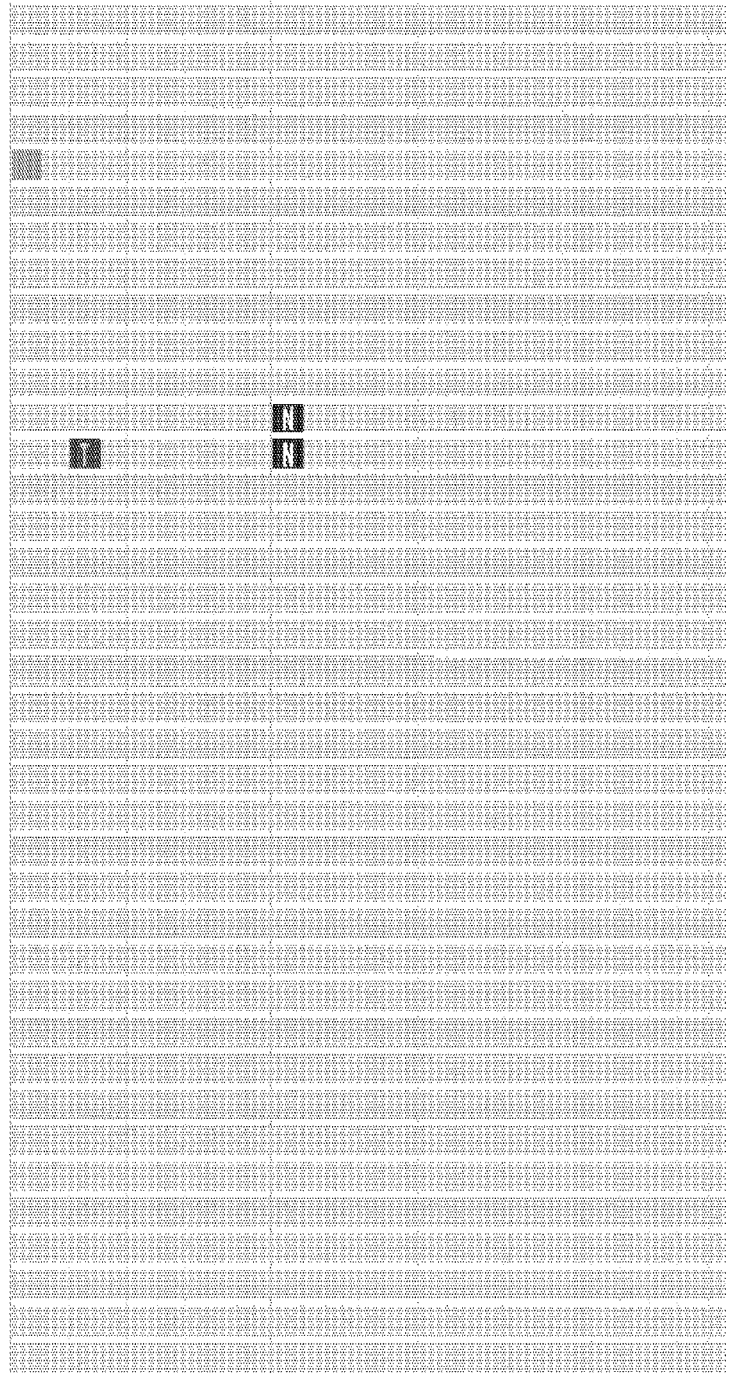
FIG. 5 is the exemplary display view of FIG. 4 at a kilobase zoom level.

FIG. 5 is viewing approximately 2 megabases (2 million bases) at a kilobase zoom level while the number of pixels is maintained constant. As a result, both the bamserver and the visualization engine have downsampled the data being drawn. The bamserver has reduced the amount of copy-number data it provides the visualization engine, and the visualization engine has ignored the raw data track because viewing would be impractical. In addition, the visualization engine has begun to summarize one of the variant tracks (the bottom-most track) by producing a graphical histogram at the top. Finally, the visualization engine has averaged together the multiple datapoints for the copy-number variation that sit beneath each pixel to produce a more accurate image.

Figures 3, 4, 5, 6:
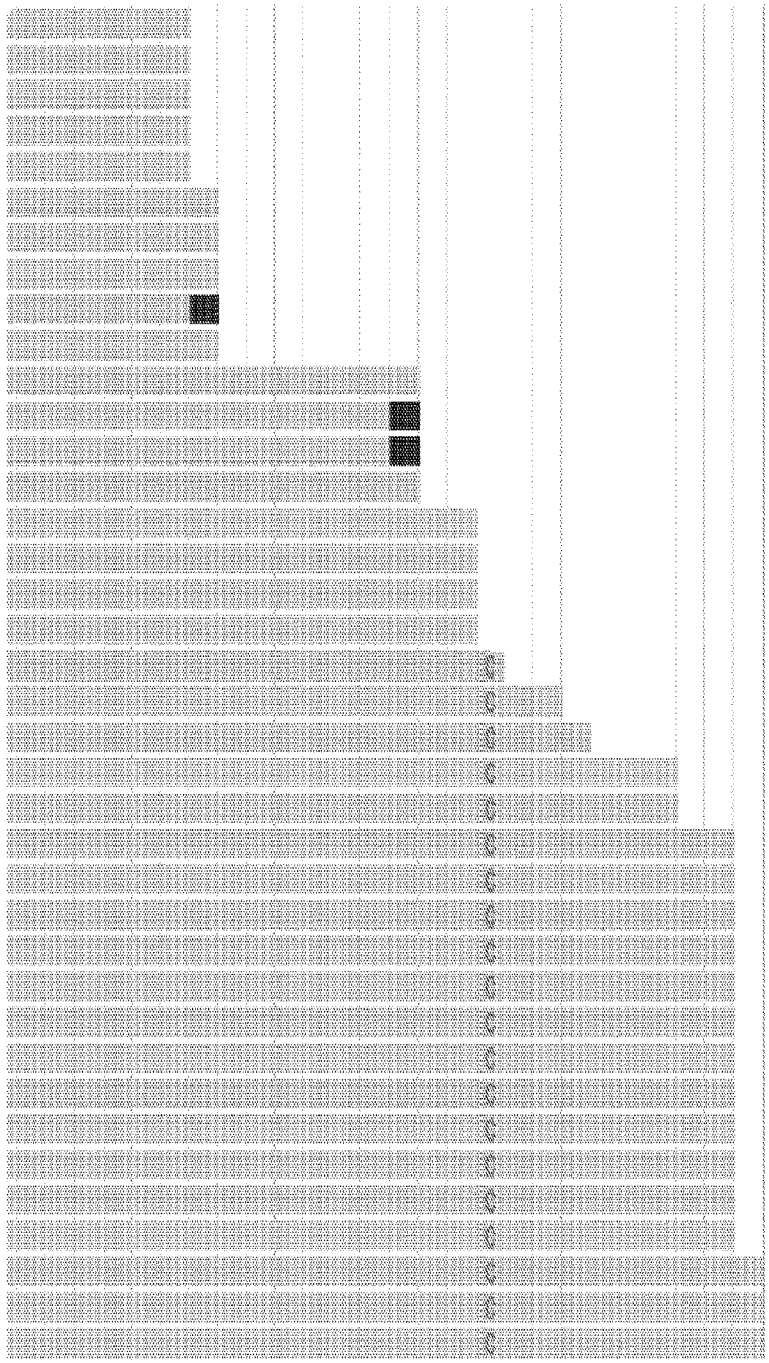
FIG. 6 is the exemplary display view of FIG. 5 at a chromosome zoom level.
Figures 3, 4, 5, 6, 7:
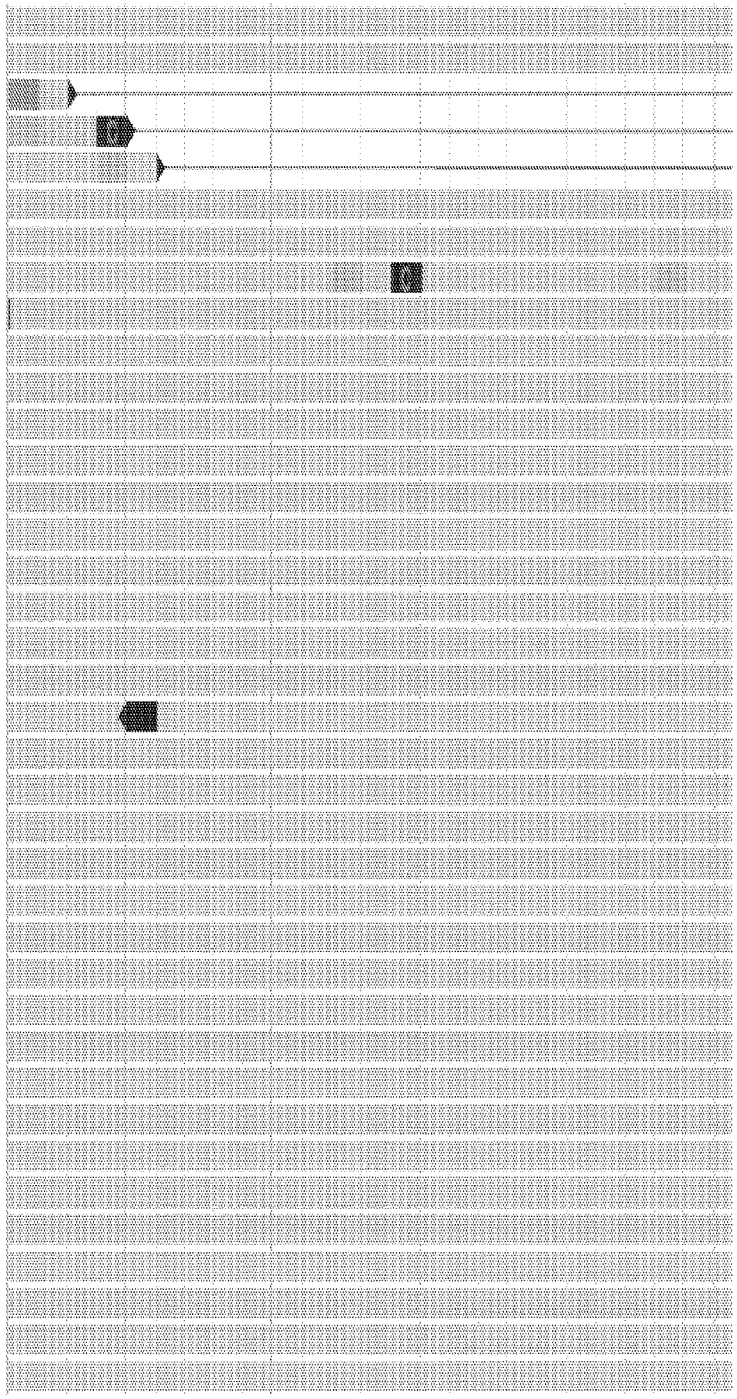
Figures 3, 4, 5, 6, 7, 8:
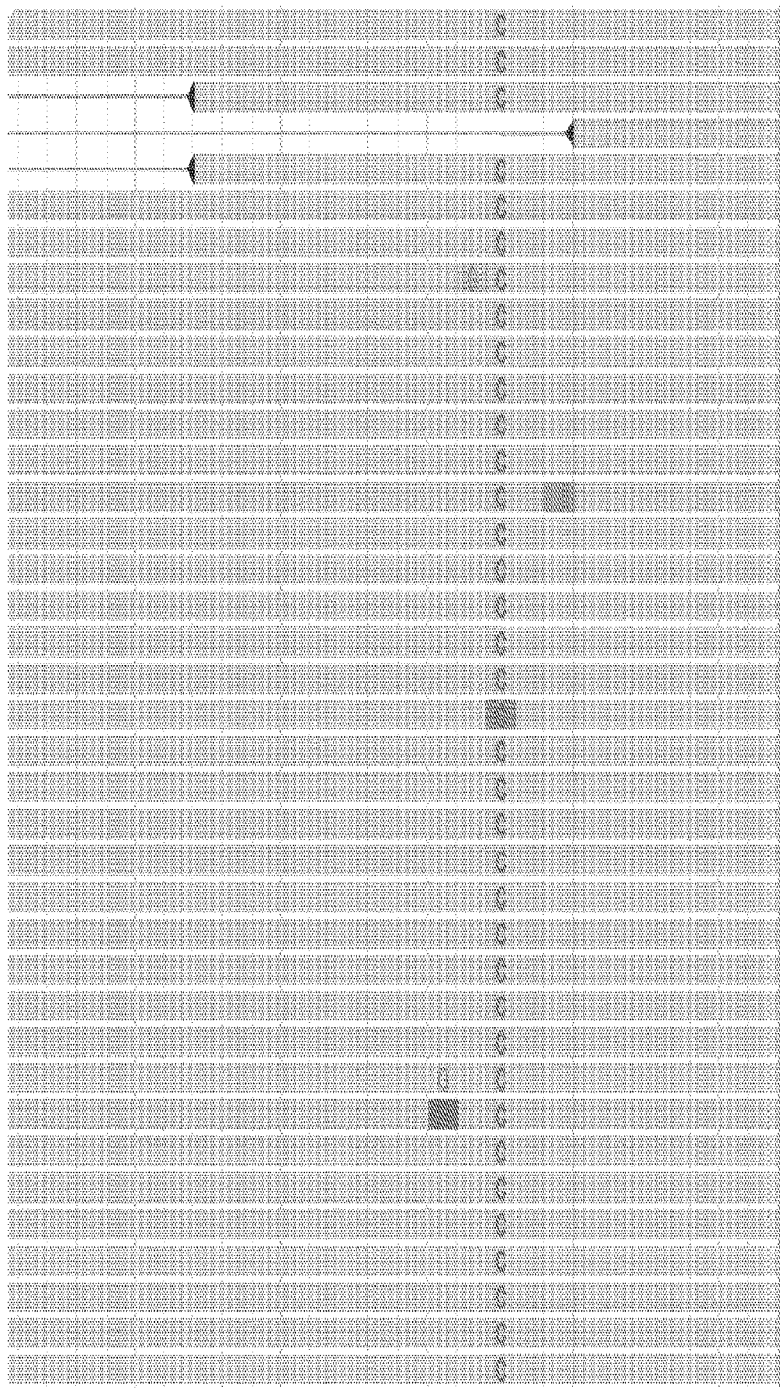
Figures 3, 4, 5, 6, 7, 8, 9:
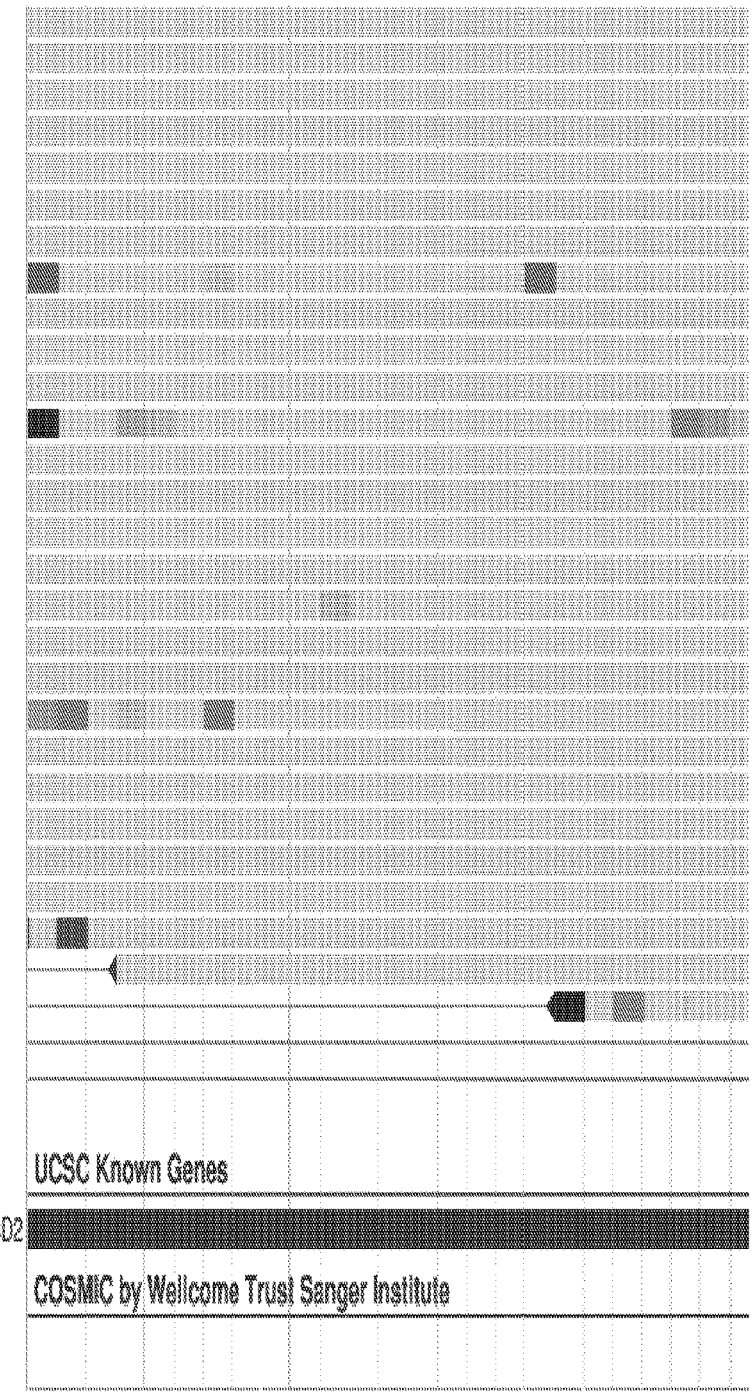
Figures 3, 4, 5, 6, 7, 8, 9, 10:
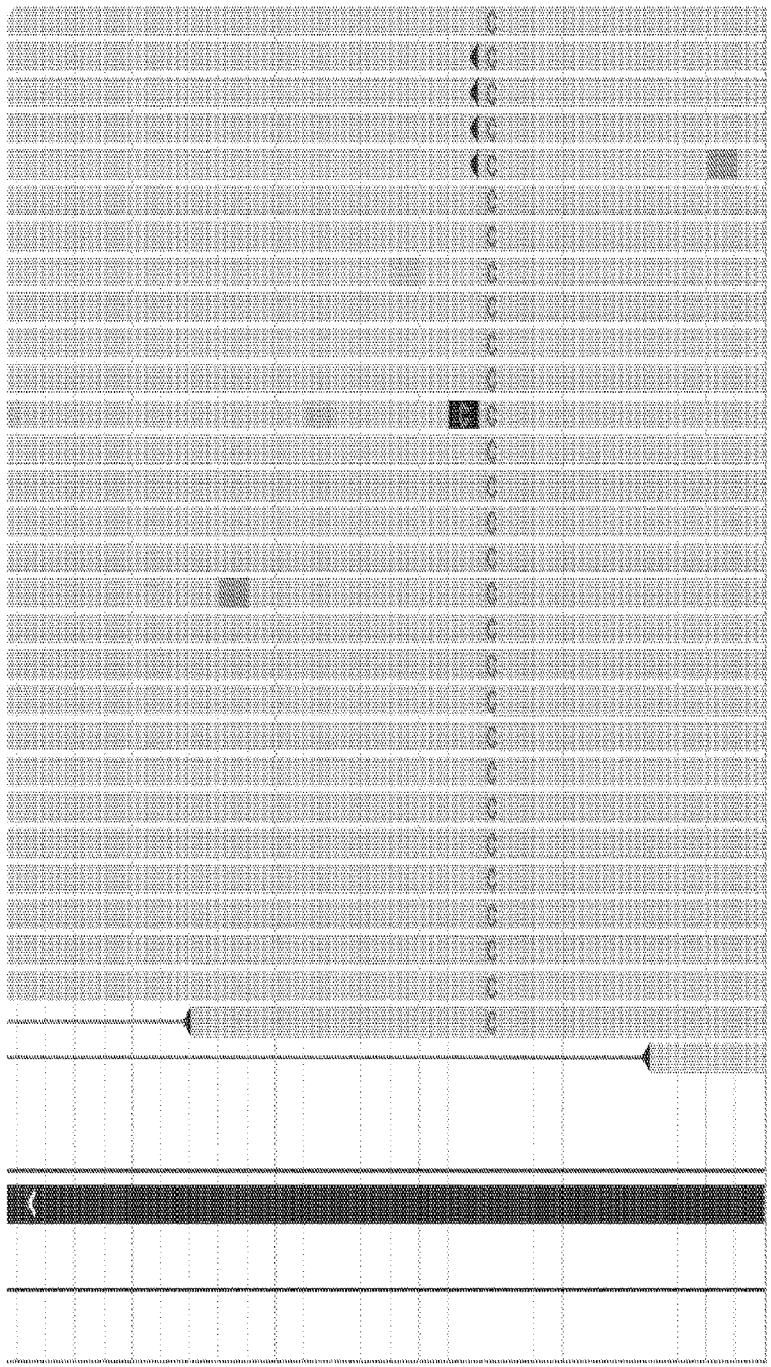
Figures 1, 4:
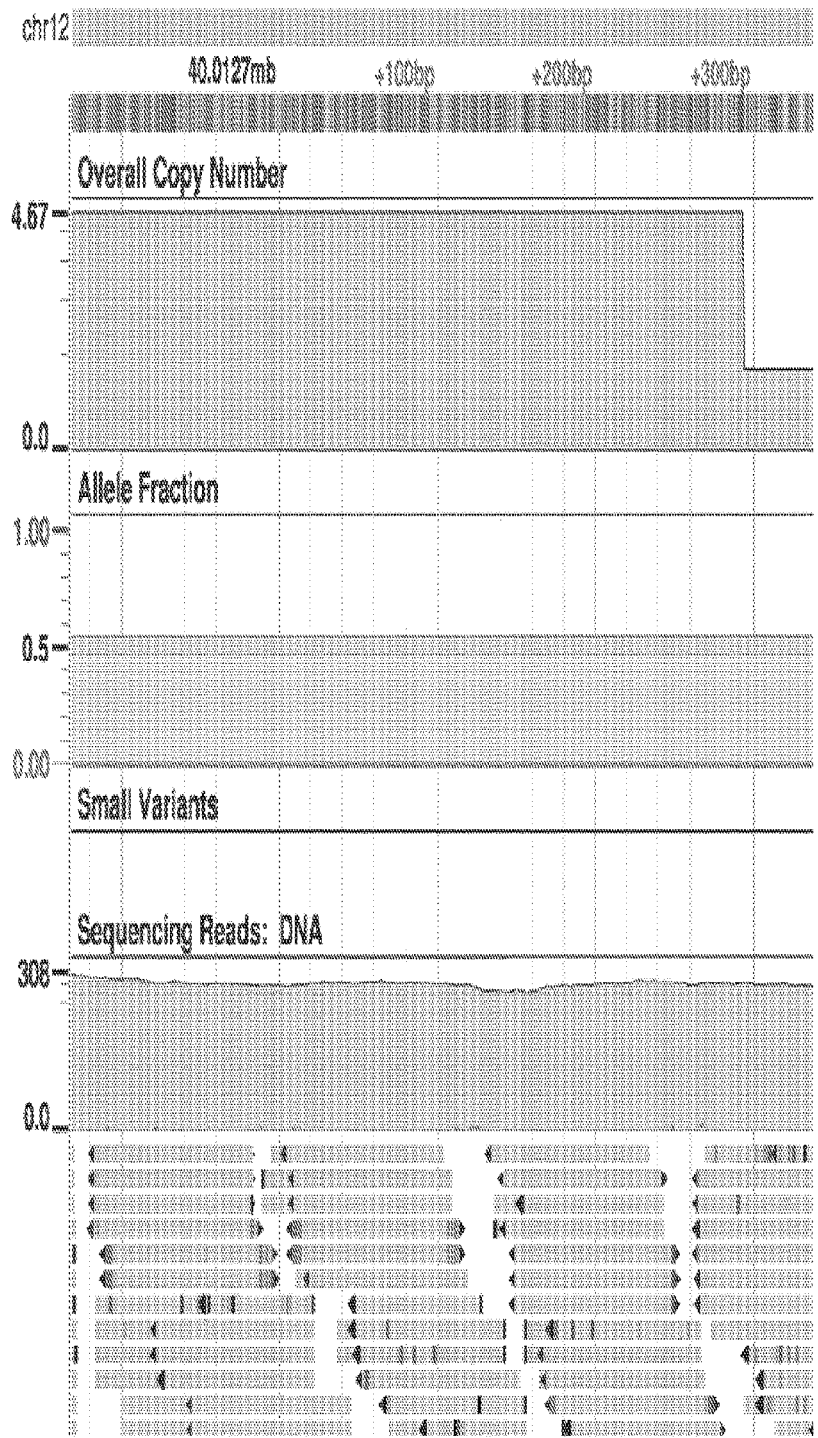
Figures 2, 4:
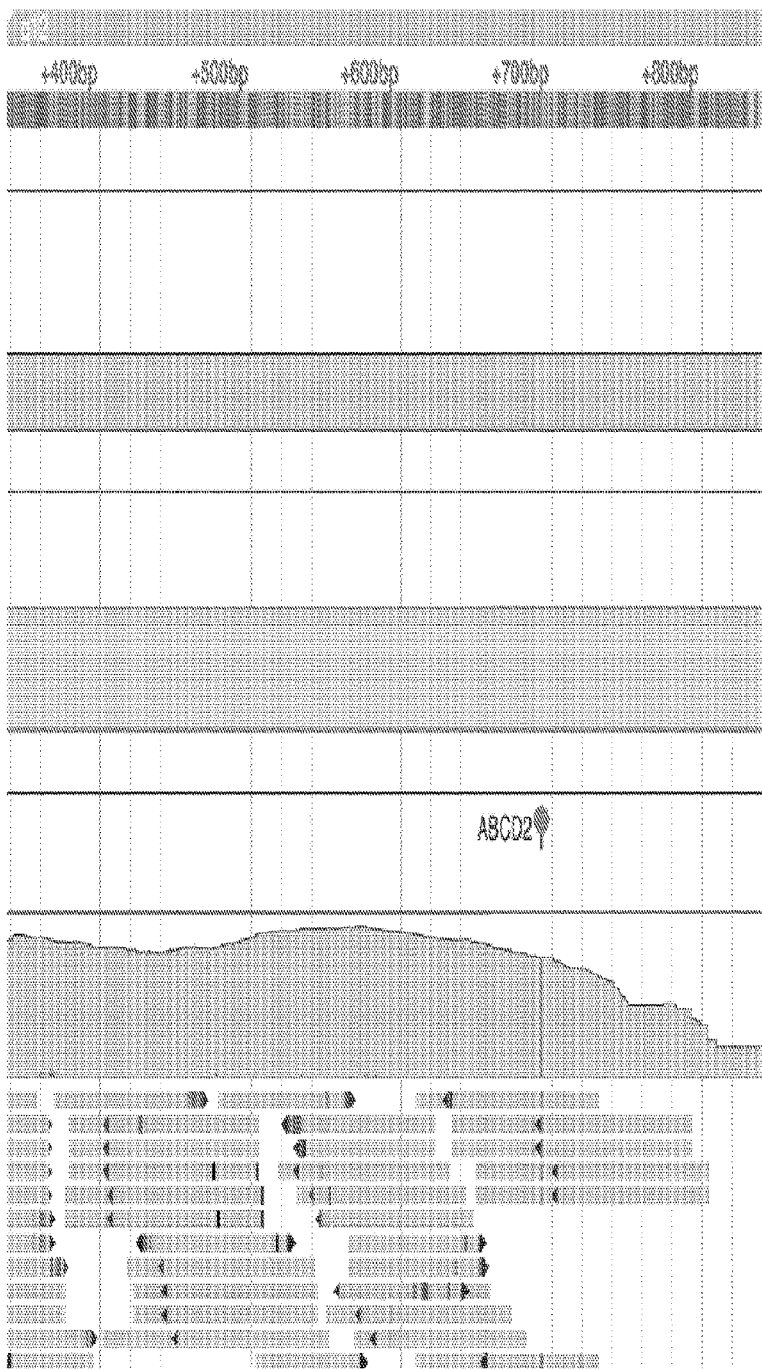
Figures 3, 4:
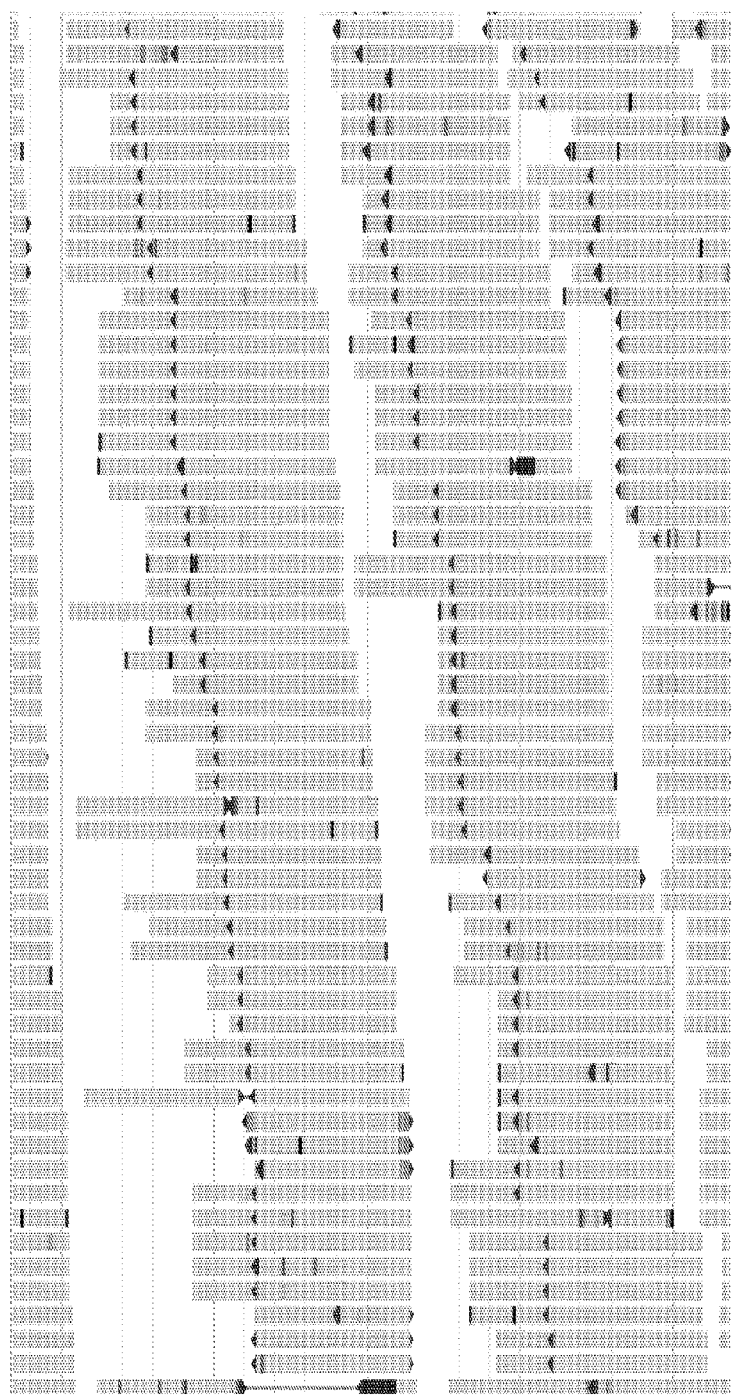
Figure 4:
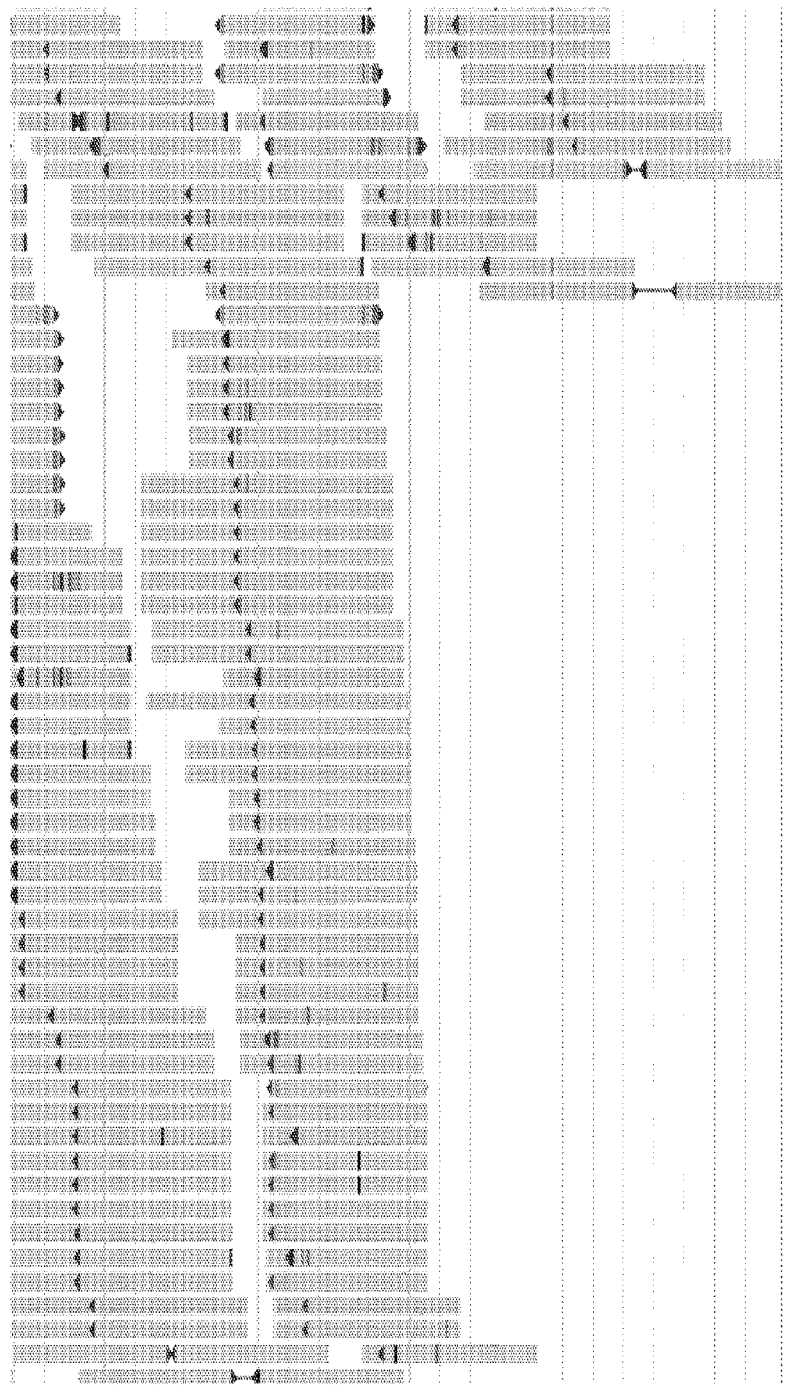
Figures 4, 5:
Figures 4, 5, 6:
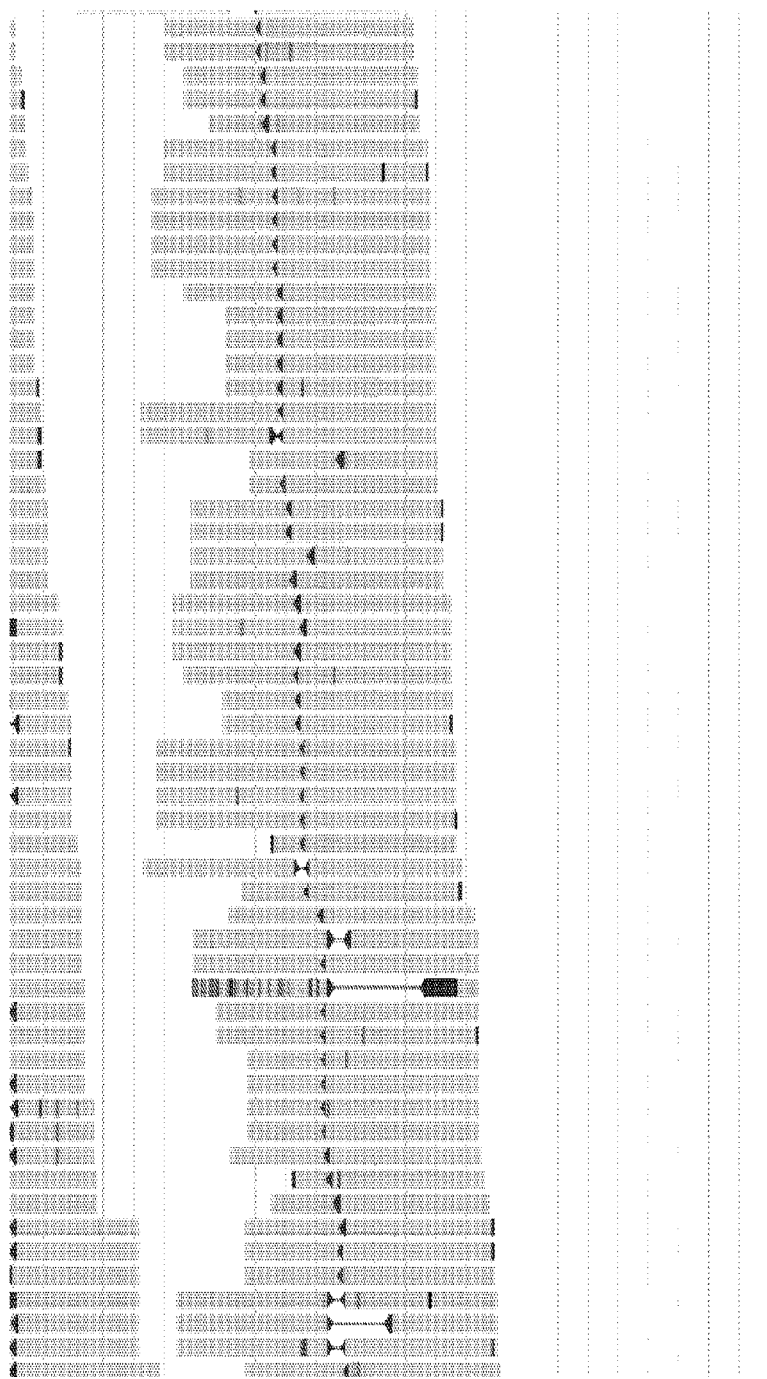
Figures 4, 5, 6, 7:
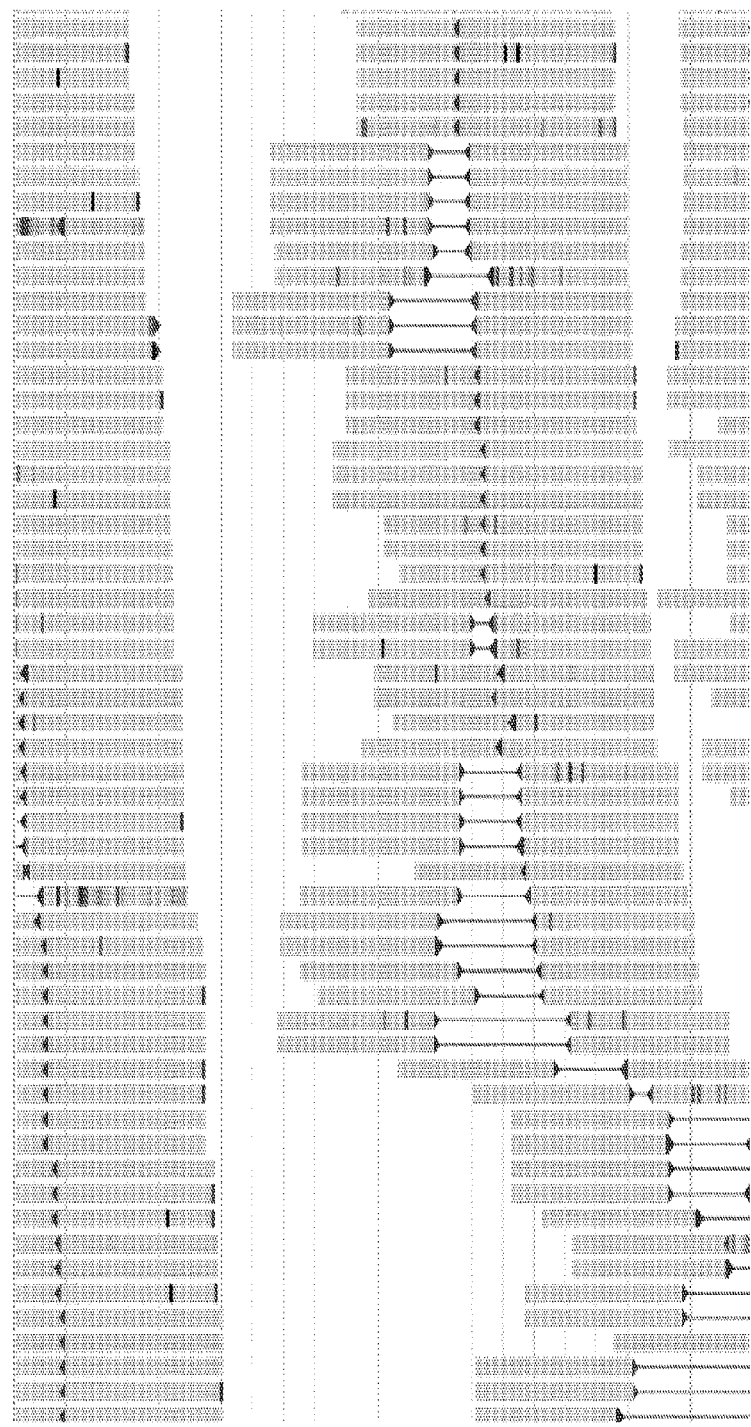
Figures 4, 5, 6, 7, 8:
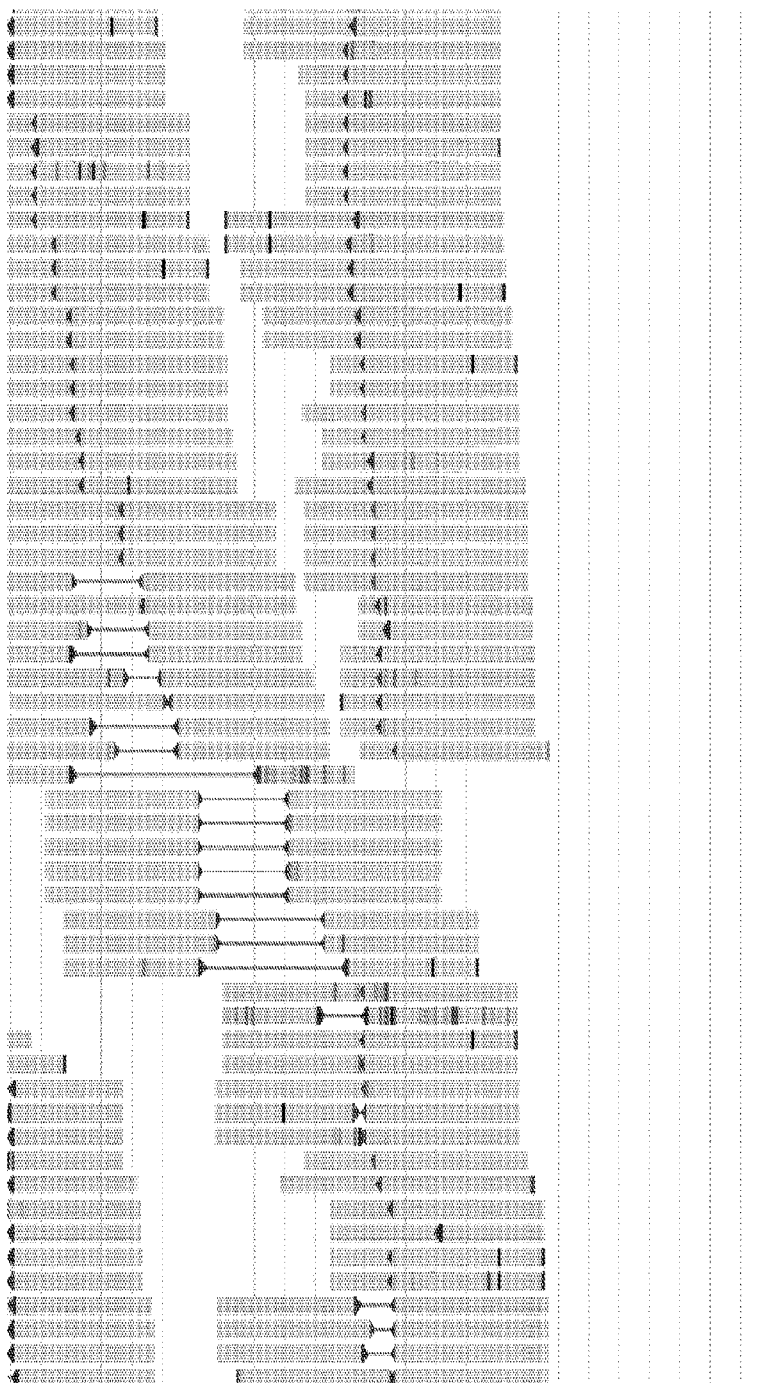
Figures 4, 5, 6, 7, 8, 9:
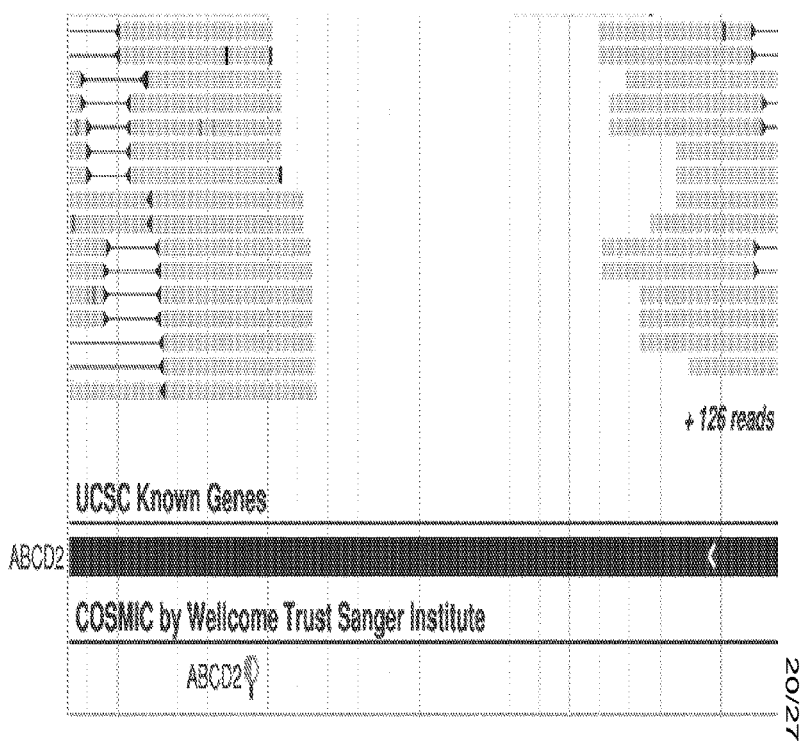
Figures 4, 5, 6, 7, 8, 9, 10:
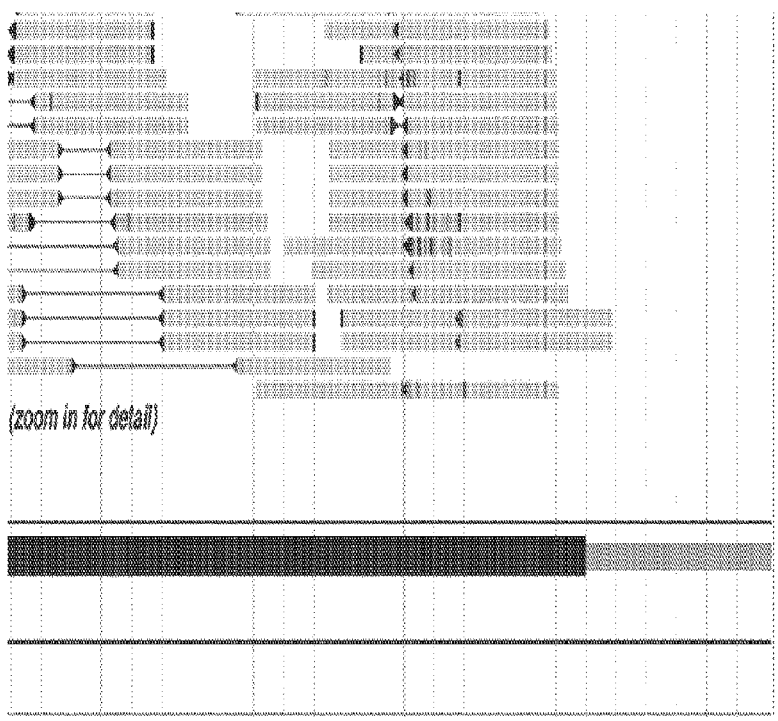
Figures 1, 5:
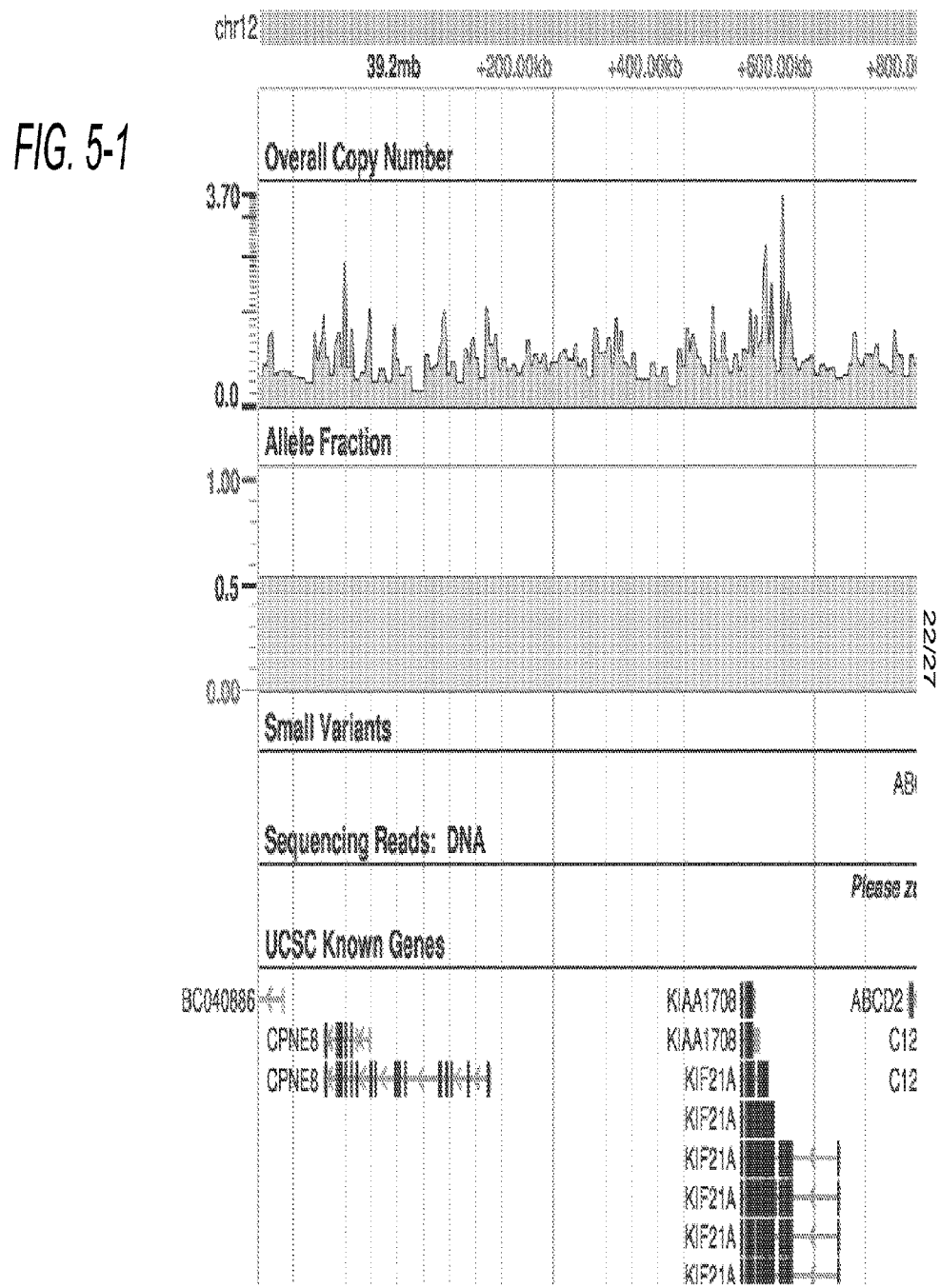
Figures 2, 5:
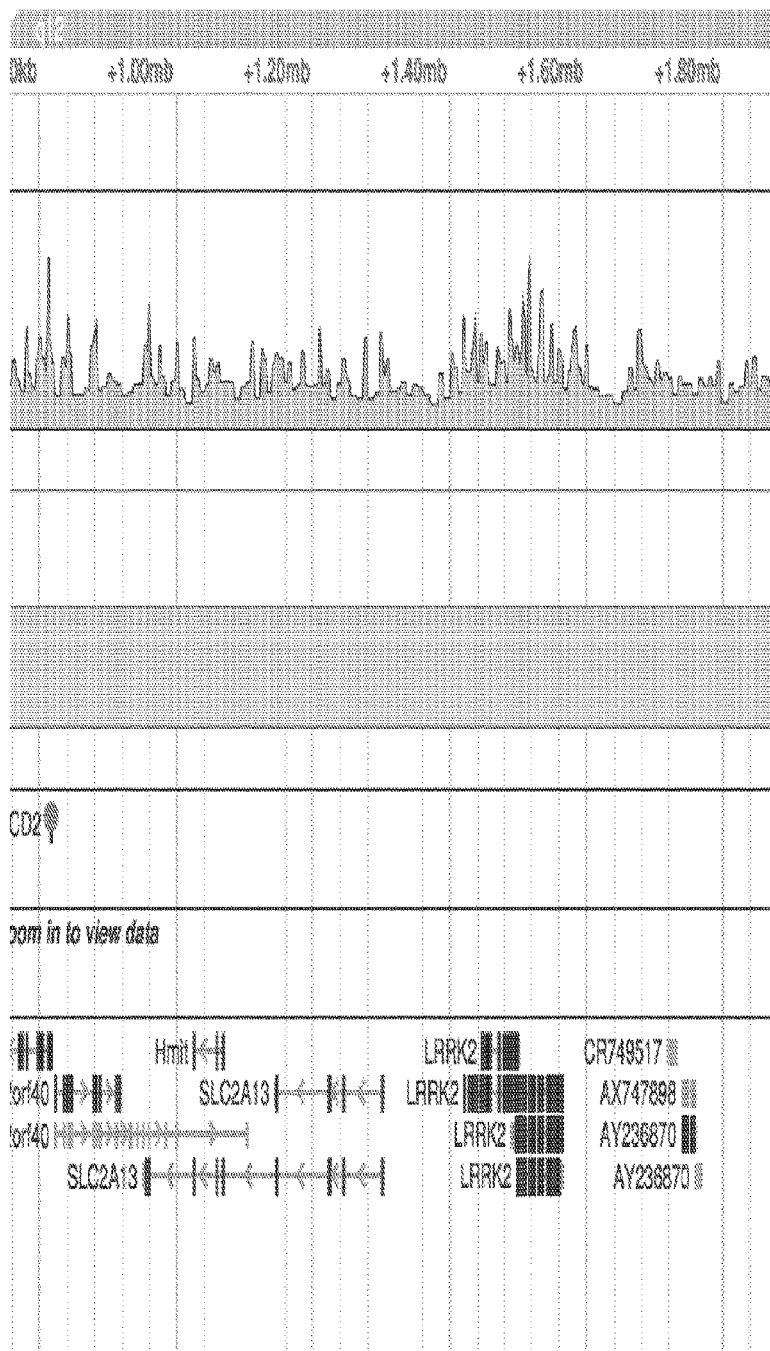
Figures 3, 5:
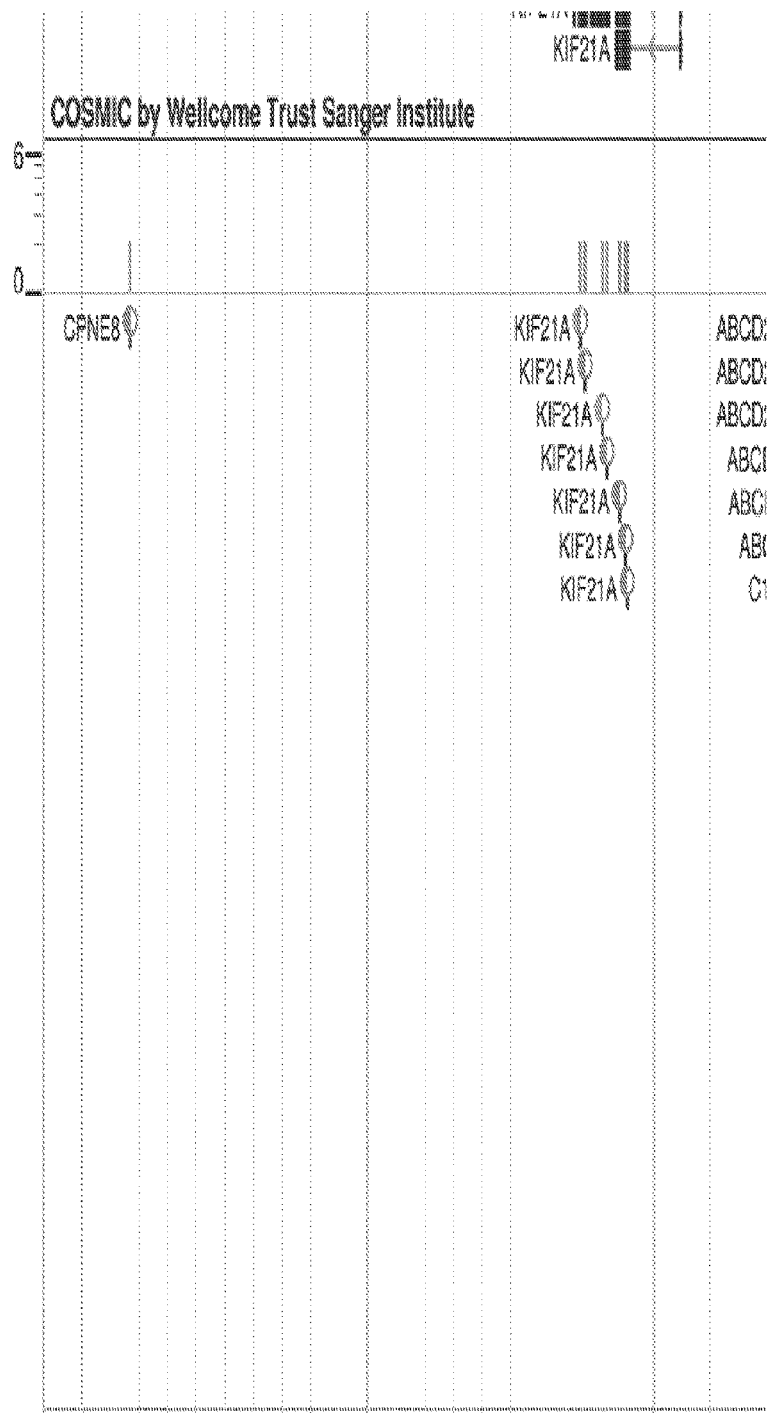
Figures 4, 5:
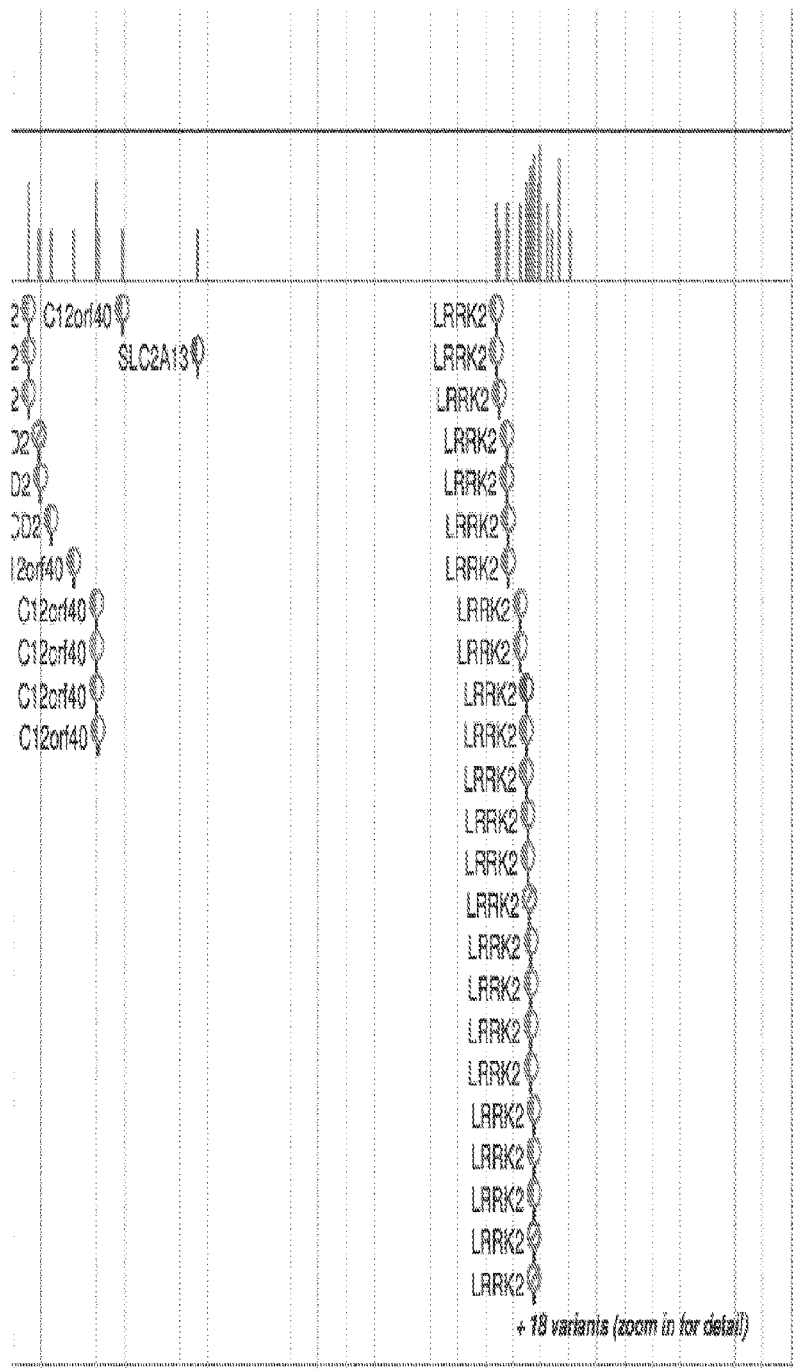
Figures 1, 6:
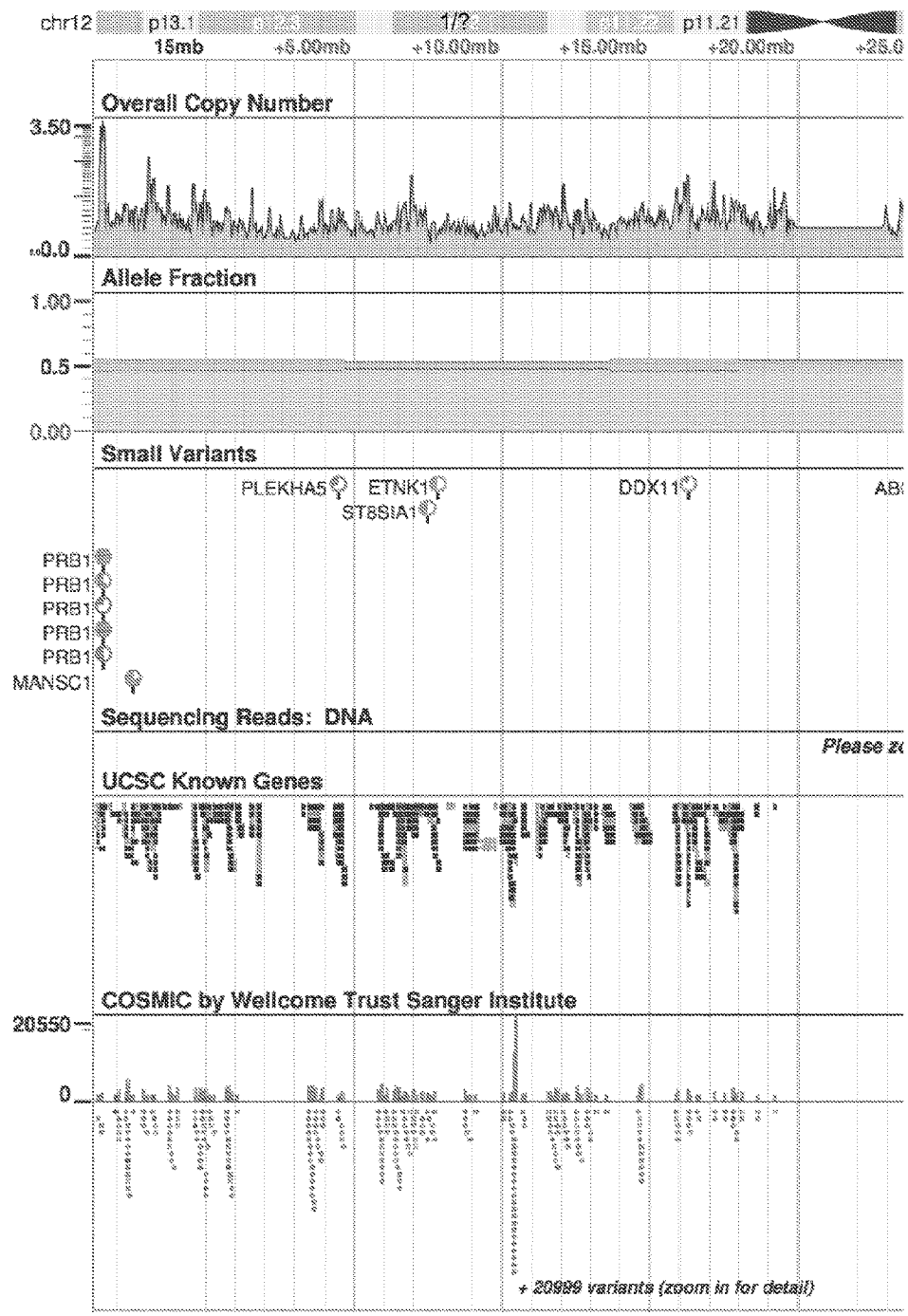
Figures 2, 6:
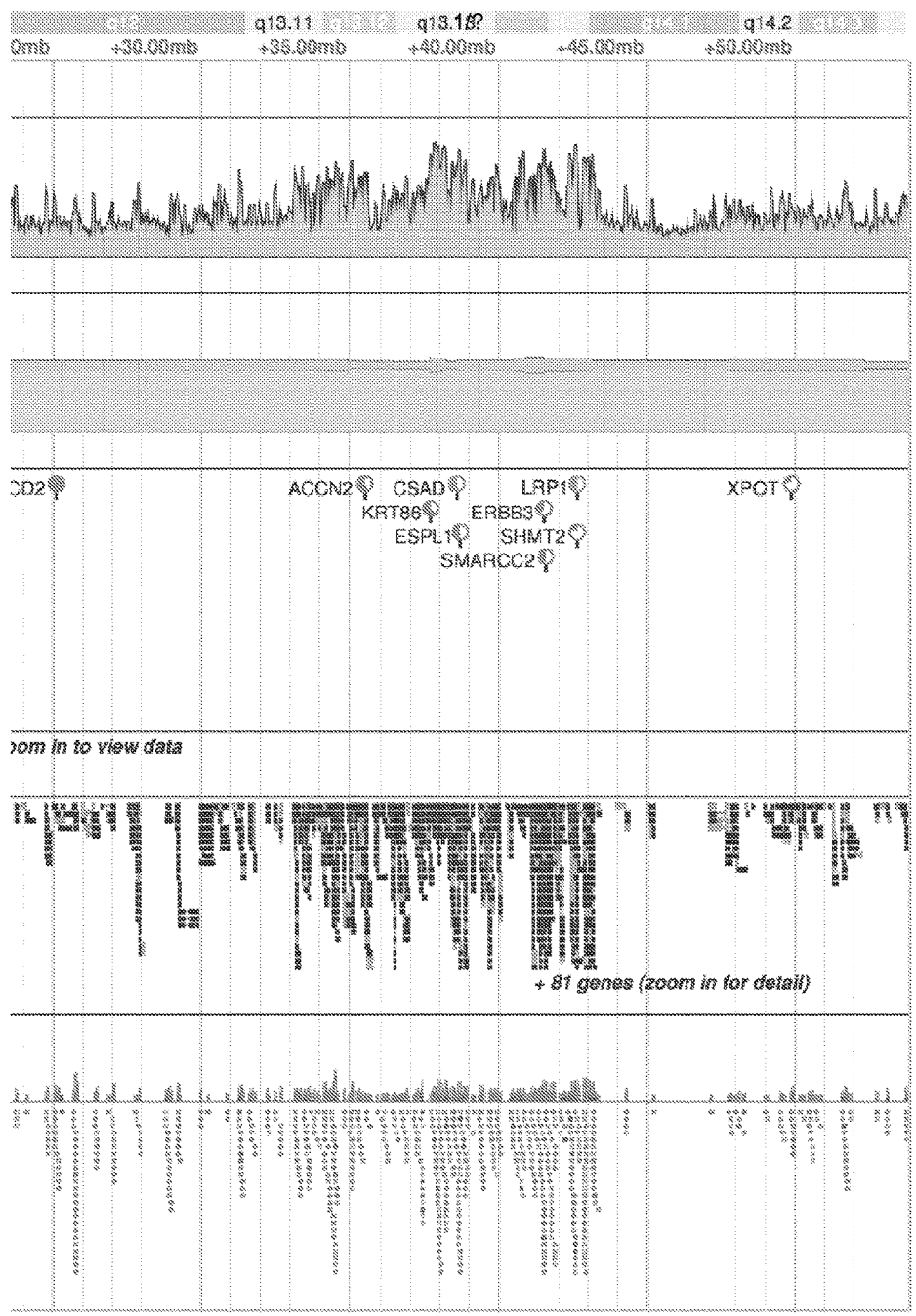

The final resolution, FIG. 6, represents all of chromosome 12 at a chromosome zoom level. All of the previous downsampling is occurring at this resolution, with additional downsampling being down to remove the text and display a more graphical representation of both the UCSC Known Gene and COSMIC variant tracks at the bottom of the image. While one clear example has been represented in these diagrams, this engine provides a framework for dynamic visualization that is not limited to pre-determined and pre-drawn resolution levels, and furthermore can accommodate many different types of underlying data beyond what has been shown here.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where a definition or use of a term in an incorporated reference is inconsistent or contrary to the definition of that term provided herein, the definition of that term provided herein applies and the definition of that term in the reference does not apply. Where the specification claims refers to at least one of something selected from the group consisting of A, B, C . . . and N, the text should be interpreted as requiring only one element from the group, not A plus N, or B plus N, etc.

What is claimed is:
1. A genomic visualization system comprising:
   an indexed genomic database configured to store a sequence object representative of a genomic region, the sequence object comprising a plurality of scale-relevant annotations; and
   a scaling engine coupled with the indexed genomic data storage and configured to:
      adjust scale-relevant information derived from the scale-relevant annotations of the sequence object as a function of a user selected zoom level;

dynamically generate a genomic display object for the sequence object, wherein the genomic display object is representative of the scale-relevant information based on the zoom level, wherein dynamic generation comprises an alteration of presented visualization of the sequence object;

wherein the scaling engine dynamically and automatically downsamples data comprising the genomic display object before the downsampled data is transferred to an output device, wherein the scaling engine dynamically and automatically downsamples the data in response to a request that indicates a number of data points that will be utilized by a consuming application, wherein dynamic downsampling is further based on the size of the genomic region requested and knowledge about the graphical resolution of an output device with which the data will be displayed; and transfer the downsampled data to the output device to present the downsampled data comprising the genomic display object to a user.

2. The system of claim 1, wherein the sequence object has a SAM/BAM or BAMBAM format, or wherein the genomic region is one of the following: a whole genome, a chromosome, a chromosomal fragment, and an allele.

3. The system of claim 1, wherein downsampling is accomplished by a first mechanism that requires no knowledge of underlying data and uses pre-condensed files and/or a second mechanism that requires additional information about the file type to so dynamically summarize data.

4. The system of claim 1, further comprising a bamserver operating as the scaling engine.

5. The system of claim 4, further comprising a plurality of bamservers.

6. The system of claim 1, further comprising a visualization server operating as the scaling engine.

7. The system of claim 6, further comprising a plurality of visualization servers.

8. The system of claim 1, wherein the output device comprises at least one of the following: a display, a browser, a printer, a 3D printer, and a speaker.

9. The system of claim 1, wherein the scaling engine is further configured to adjust the scale-relevant information by downsampling based on the zoom-level.

10. The system of claim 9, wherein the scaling engine is further configured to downsample as a function of data density derived from the zoom-level.

11. The system of claim 1, wherein the scaling engine is further configured to determine the zoom level.

12. The system of claim 11, wherein the scaling engine is further configured to summarize a full data set of the sequence object according to the zoom level.

13. The system of claim 1, wherein the scaling engine is further configured to derive the scale-relevant information from differences in scale-relevant annotations in different sequence objects.

14. The system of claim 1, wherein the sequence object comprises a reference sequence object.

15. The system of claim 14 wherein the reference sequence object is selected from the group consisting of raw sequence data, sequence data from homo statisticus, and sequence data from a specified point in time.

16. The system of claim 1, wherein the sequence object comprises a differential sequence object with respect to a reference genomic region.

17. The system of claim 16 wherein the reference genomic region is from homo statisticus or specific to a point in time.

18. The system of claim 1, wherein the scale-relevant annotations include at least one of the following: genomic structure information, genomic change information, disease information, gene relevant information, differential information relative to a reference sequence, and metadata.

19. The system of claim 18, wherein the genomic structure includes at least one of the following: chromosome identification, location within a chromosome, and an allele.

20. The system of claim 18, wherein the genomic change information includes at least one of the following: a mutation, a translocation, an inversion, a deletion, a repeat, and a copy number.

21. The system of claim 18, wherein the disease information includes at least one of the following: a type of disease, a status of disease, and a treatment option for the disease.

22. The system of claim 18, wherein the gene relevant information comprises raw sequence data or processed sequence data, gene identification, information on gene regulation, and information of association of the gene with a disease.

23. The system of claim 18, wherein the metadata includes at least one of the following: patient identification, facility identification, physician identification, and insurance information.

24. The system of claim 1, further comprising a genomic graphic library configured to store a graphic object representative of scale-relevant annotations.

25. The system of claim 24, wherein the scaling engine is further configured to map the scale-relevant information to graphic objects from graphic library according to the zoom level.

26. The system of claim 25, wherein the genomic display object comprises the mapped graphic objects.

* * * * *